United States Patent [19]

Barnea

[11] Patent Number: 6,037,446
[45] Date of Patent: *Mar. 14, 2000

[54] GESTATIONAL AGENTS FOR CONTROLLING CELL PROLIFERATION

[75] Inventor: Eytan Barnea, Cherry Hill, N.J.

[73] Assignee: EnVision, Cherry Hill, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/783,267

[22] Filed: Jan. 15, 1997

Related U.S. Application Data

[60] Division of application No. 08/373,082, Jan. 17, 1995, Pat. No. 5,648,340, which is a continuation-in-part of application No. 08/184,509, Jan. 19, 1994, abandoned, which is a continuation of application No. 07/785,966, Oct. 31, 1991, abandoned.

[30] Foreign Application Priority Data

Nov. 28, 1990 [IL] Israel ......................................... 096499

[51] Int. Cl.$^7$ .......................... A61K 38/02; A61K 38/17; C07K 2/00; C07K 14/47

[52] U.S. Cl. .............................. 530/300; 530/853; 514/21

[58] Field of Search .................................... 424/582, 538; 514/21; 530/300, 344, 350, 423, 839, 850, 851, 853

[56] References Cited

U.S. PATENT DOCUMENTS

| | | | |
|---|---|---|---|
| 4,708,948 | 11/1987 | Iwata et al. | 514/2 |
| 4,806,492 | 2/1989 | Shoyab et al. | 436/547 |
| 4,908,206 | 3/1990 | Schafer et al. | 424/553 |
| 4,945,055 | 7/1990 | Kuehl et al. | 435/226 |
| 5,196,334 | 3/1993 | Rowley et al. | 530/339 |
| 5,648,340 | 7/1997 | Barnea | 514/21 |

FOREIGN PATENT DOCUMENTS

| | | |
|---|---|---|
| 341734 | 11/1989 | European Pat. Off. . |
| 2451193 | 10/1980 | France . |
| 59-078694 | 5/1984 | Japan . |
| 2215730 | 8/1990 | Japan . |
| 8504397 | 1/1985 | WIPO . |

OTHER PUBLICATIONS

Wyngaarden et al. Cecil Textbook of Medicine, 19$^{th}$ ed. W.B. Saunders Co. (Phila) pp. 727–730, 2218, 1988.
Avigdor et al., 1992, Reprod. Toxicol.6:363–366.
Massague & Laiho, 1992, in Growth Factors of the Vascular and Nervous Systems, eds. Lenfant, C., Paoletti, R. & Albertini, A. (Karger, Basel Munchen), pp. 6–16.
Shurtz–Swirski et al., 1992, Human Reprod. 7:300–304.
Barnea & Avigdor, 1991, Gynecol. Obstet. Invest. 32:4–9.
Letnansky, 1991, AntiCancer Research 11:981–986.
Pagliacci et al., 1991, Endocrinol. 129:2555–2562.
Sariola et al., 1991, Science 254:571–573.
Shurtz–Swirski et al., 1991, Placenta 12:521–531.
Barnea & Avigdor, 1990, J. Steroid Biochem 35:327–331.
Barnard et al., 1990, Biochim. Biophys. Acta 1032:79–98.
Nahhas & Barnea, 1990, Am. J. Reprod. Immunol. 22:105–108.
Plowman et al., 1990, Mol. Cell. Biol. 10:1969–1981.
Barnea et al., 1989, Placenta 10:331–344.
Barnea and Kaplan, 1989, J. Clin. Endocrinol. Metab. 69:215–217.
Berthois et al., 1989, Biochem. Biophys. Res. Commun. 159:126–131.

(List continued on next page.)

*Primary Examiner*—Jeffrey E. Russel
*Attorney, Agent, or Firm*—Baker Botts LLP

[57] ABSTRACT

The present invention relates to substantially purified agents normally expressed during mammalian pregnancy that may be used to control the proliferation of cells, and, in particular, provides for proliferative agents as well as antiproliferative agents. The antiproliferative agents may be used to limit undesirable proliferation of cells, for example, in the treatment of cancer. The proliferative agents may be utilized to increase cell proliferation and may be used, for example, in the treatment of infertility.

2 Claims, 29 Drawing Sheets

OTHER PUBLICATIONS

Harris et al., 1989, Protein Purification Methods, IRL Press, pp. 9–10, 57–60.

Sanyal et al., 1989, Am. J. Obstet. Gynecol. 161:446–453.

Alley et al., 1988, Cancer Res. 45:589–601.

Clark, 1988, in early Pregnancy Loss Mechanisms and Treatment, eds. Beard, R.W. & Shapr, F. (RCOG London), pp. 215–227.

Pines et al., 1988, J. Cellular Biochem. 37:119–129.

Barnea et al., 1986, Arch. Gynecol. 237:187–190.

Pines et al., 1986, Biochem. Pharmacol. 35:3639–3641.

Pines et al., 1986, Bone and Mineral 1:15–26.

Cole et al., 1985, in "Monoclonal Antibodies and Cancer Therapy," Alan R. Liss, Inc. pp. 77–96.

Pines et al., 1985, Proc. Natl. Acad. Sci. U.S.A. 82:4095–4099.

Ramsay et al., 1985, Biol. Neonate 47:42.

Resnitzky et al., 1985, Leukemia Res. 9:1519–1528.

Roberts et al., 1985, Proc. Natl. Acad. Sci. U.S.A. 82:119–123.

Takeda et al., 1985, Nature 314:452.

Albrecht et al., 1984, Endocrinol. 107:766.

Morrison et al., 1984, Proc. Natl. Acad. Sci. U.S.A. 81:6851.

Robertson et al., 1984, Endocrinol 114:22–31.

Taylor et al., 1984, Res. Vet. Sci. 35:22.

Kozbor et al., 1983, Immunology Today 4:72–79.

Massague, 1983, J. Biol. Chem. 258:13614–13620.

Teng et al., 1983, Proc. Natl. Acad. Sci. U.S.A. 80:7308–7312.

Aspillaga et al., 1982, Am. J. Obstet. Gynecol. 147:903.

Olsson et al., 1982, Meth. Enzymol. 92:3–16.

Majeska et al., 1980, Endocrinol. 107:1494–1503.

Steinberg et al., 1978, Cell 13:19–32.

Moore, 1977, in "The Developing Human," second edition, W.B. Saunders Company, Philadelphia, pp. 33–43.

Kohler and Milstein, 1975, Nature 256:495–497.

Delf, 1957, Obstet. Gynecol. 9:1–24.

FIG.27A    FIG.27B
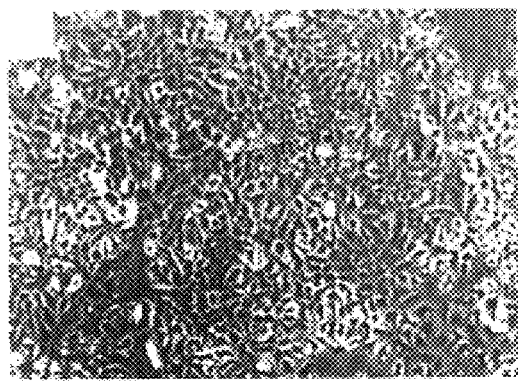 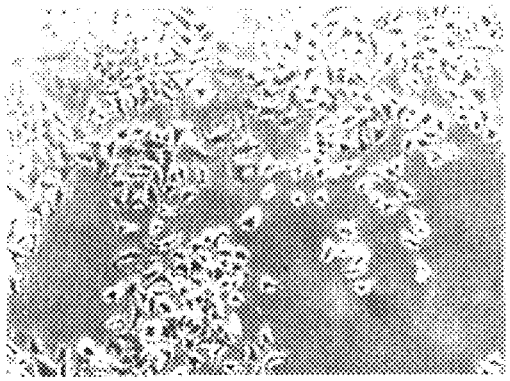
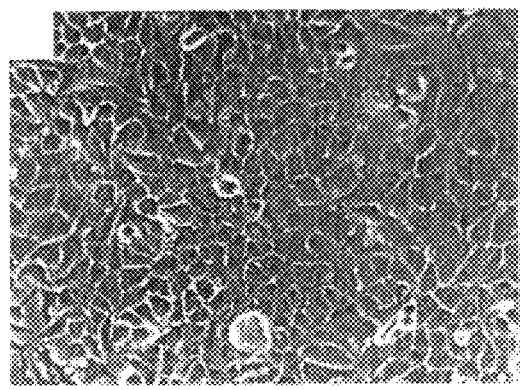 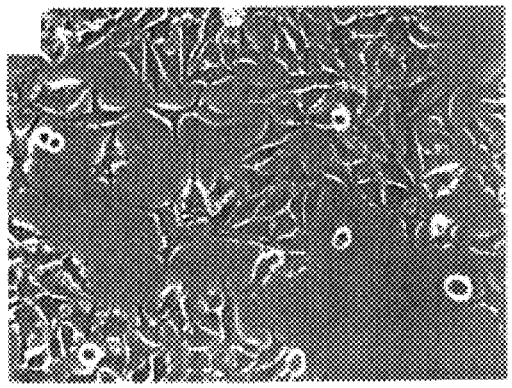
FIG.27C    FIG.27D

GESTATIONAL AGENTS FOR CONTROLLING CELL PROLIFERATION

1. INTRODUCTION

This application is a divisional of U.S. Ser. No. 08/373,082, now U.S. Pat. No. 5,648,340, filed Jan. 17, 1995, which is a continuation-in-part of U.S. Ser. No. 08/184,509, filed Jan. 19, 1994 (abandoned), which is a continuation of U.S. Ser. No. 07/785,966, filed Oct. 31, 1991 (abandoned).

The present invention relates to substantially purified agents normally expressed during mammalian pregnancy that may be used to control the proliferation of cells, and, in particular, provides for proliferative agents as well as antiproliferative agents. The antiproliferative agents may be used to limit undesirable proliferation of cells, for example, in the treatment of cancer. The proliferative agents may be utilized to increase cell proliferation and may be used, for example, in the treatment of infertility.

2. BACKGROUND OF THE INVENTION

Human gestation is divided into two developmental stages: the embryonic period, which extends from conception to the end of the eighth week, followed by the fetal period, which lasts until parturition. During the embryonic period, the developing embryo undergoes numerous changes in order to recreate the human blueprint and to establish the maternal connection necessary for its survival. The genesis of virtually all essential structures occur prior to the eighth week of development. During the fetal period, these structures grow and become more elaborate (see, for review, Moore, 1977, in "The Developing Human," second edition, W. B. Saunders Company, Philadelphia).

Very early in the embryonic period, the fertilized egg, or zygote, undergoes a number of cell divisions to form a ball of about 15 small cells, called the morula. The morula enters the uterus and develops an inner cavity, thereby becoming a blastocyst consisting of (1) an inner cell mass which gives rise to the embryo; (2) a blastocyst cavity; and (3) an outer layer of cells, called the trophoblast. About five or six days after conception, the blastocyst attaches to the endometrial epithelium of the uterus and the trophoblastic cells invade the uterine wall.

With time, the actively erosive trophoblast invades the endometrial stroma, and the blastocyst is gradually engulfed by the endometrium (Id., p. 33). The trophoblast differentiates into two types: cytotrophoblast and syncytiotrophoblast. The syncytiotrophoblast is adjacent to the developing embryo and becomes a multinucleated protoplasmic mass in which no cell boundaries are discernible (Id., p. 34). Isolated spaces, called lacunae, appear in the syncytiotrophoblast at about day 9 and become filled with a fluid consisting of maternal blood and secretions. This fluid, or embryolymph, provides nutrition to the developing embryo and marks the beginning of the uteroplacental circulation. Eventually, the endometrium forms the maternal part, and the trophoblast forms the fetal part, of the placenta (Id., p. 36).

Once the primitive placental circulation is established, the embryo begins to develop at astonishing speed. By 20 days, the brain and spinal cord have begun to form. At about 22 days, the embryonic heart begins to beat. At 27 days arm and leg buds have appeared. By 30 days, the eyes and nose are forming. By 40 days, the arms are bent at the elbow, early fingers and ears are apparent, and the embryo is only one centimeter long.

This period of rapid development is accomplished by a carefully regulated program of cell division and differentiation which is, at this time, incompletely understood. An interest in the signals involved in initiating or terminating embryonic development has prompted analysis of hormones and cytokines associated with placental, embryonic, or fetal tissue. A brief list of some results of such studies follows.

Two well-documented protein products of the placenta are (1) human chorionic gonadotrophin (hCG) and (2) human chorionic somatomamotropin (hCS), also known as human placental lactogen (hPL) (Id., p. 105). hCG is produced by the trophoblast, and acts to prevent degeneration of the corpus luteum, an ovarian structure that produces progesterone. During early pregnancy, circulating hCG levels increase linearly until eight weeks of gestation, reaching a plateau at between nine and ten weeks of gestation, and thereafter declining until term. This secretory pattern is considered to be an important indicator of normal trophoblast development. In fact, if circulating hCG levels continue to increase beyond ten weeks of gestation, trophoblastic neoplasia, such as a hydatiform mole, should be suspected (Delf, 1957, Obstet. Gynecol. 9:1). On the other hand, a premature plateau and decrease in hCG level generally indicate early pregnancy failure (Aspillaga et al., 1982, Am. J. Obstet. Gynecol. 147:903).

Yoshida, Japanese Patent No. 59078694, May 7, 1984, reports the identification of a cobalt-activated substance in fetal or placental tissue which inhibits the action of a carcinogenic protein-forming enzyme.

Japanese Patent No. 2215730, Aug. 28, 1990, reports the isolation of the cytokine transforming growth factor-beta (TGF-beta) from human placenta.

Massague (1983, J. Biol. Chem. 258:13614–13620) reports the binding of epidermal growth-factor like transforming growth factor to epidermal growth factor receptors in human placenta membranes.

Roberts et al. (1985, Proc. Natl. Acad. Sci. U.S.A. 82:119–123) reports that TGF-beta may be isolated from human placenta, among other tissues. It was observed that the response of cells to TGF-beta appeared to be bifunctional, in that TGF-beta was able to stimulate reversible transformation of murine fibroblasts, but was also able to inhibit anchorage-dependent growth of normal rat kidney fibroblasts and of human tumor cells by increasing cell cycle time.

Letnansky (1987, Immunology 175:68) reports the isolation and characterization of a bovine placenta protein which specifically inhibits the proliferation of tumor cells. This protein, termed decidua inhibitory factor (DIF), was estimated to have a molecular weight of about 60 kD by SDS-PAGE.

Barnea et al. (1989, Placenta 10:331–344) report that human embryonal extracts modulate placental function in the first trimester. They observed that extracts of specific tissues were capable of decreasing or, alternatively, increasing hCG secretion. In particular, water extract of embryonal lung was found to produce a twofold decrease in hCG production by placental explants; a protein having a molecular weight less than 8000 daltons appeared to be the active agent, but was not purified.

Plowman et al. (1990, Mol. Cell. Biol. 10:1969–1981) report the isolation of a gene encoding amphiregulin (AR), a cytokine that is evolutionarily related to epidermal growth factor and to transforming growth factor alpha (TGF-alpha). AR was observed to be an 84 amino acid protein capable of acting as a bifunctional growth modulator, being able to promote the growth of normal epithelial cells and also to inhibit the growth of certain carcinoma cell lines. Human placenta and ovaries were found to express significant amounts of AR-encoding RNA. The unglycosylated AR precursor minus the signal peptide was predicted to have a molecular weight of about 25,942 D.

Further toward understanding the control of development, and in addition to the above mentioned hormones and cytokines, several lines of evidence suggest that there is an interdependence in mammals between the trophoblast and the embryo. Fetal death in both sheep and rats results in a decline in placental lactogen secretion (Ramsay et al., 1985, Biol. Neonate 47:42; Albrecht et al., 1984, Endocrinol. 107:766; Taylor et al., 1984, Res. Vet. Sci. 35:22; Robertson et al., 1984, Endocrinol. 114:22). Barnea et al. (supra) investigated the possible role of embryonic visceral organs as trophoblastic function regulators by examining the effects of dilute organ extracts upon in vitro secretion of hCG, and found an hCG-suppressive effect in certain fractions. It therefore appears that the developing embryo is not entirely subject to control by its environment; rather, the embryo itself appears to play an active role in the physiology of pregnancy.

3. SUMMARY OF THE INVENTION

The present invention provides for gestational agents that may be used to control cell proliferation. It is based, at least in part, on the discovery that several agents produced by the developing embryo appear to play an important role in achieving a system of checks and balances which regulate proliferation and differentiation of cells during pregnancy.

In particular embodiments, the present invention relates to a class of mammalian embryonal proteins, termed JDK-AP, which have antiproliferative activity. Two particular species of JDK-AP protein, termed JDK-AP1 and JDK-AP2, have been substantially purified from human and pig embryos. JDK-AP1 has an apparent molecular weight of about 4.5 kd. JDK-AP2 has an apparent molecular weight of about 10.5–10.7 kd when isolated from human embryos and about 10–15 kd when isolated from porcine embryos. Both JDK-AP1 and JDK-AP2 were observed to exert an antiproliferative effect on cancer cells. According to the present invention, JDK-AP proteins, or embryonic fractions containing JDK-AP proteins, may be used for the treatment and prevention of cancer and for the prevention of pregnancy.

In alternative embodiments, the present invention provides for a class of proteins, termed JDK-P, which promote cell proliferation. In a particular, nonlimiting embodiment, the present invention provides for a substantially purified JDK-P protein having a molecular weight of less than about 3,000 daltons which is expressed in mammalian embryonal tissue and has a proliferative effect on morular cells. This gestational proliferative agent of the invention, termed GPA-1, has further been observed to increase the secretion of human chorionic gonadotrophin by placental explants, to promote the development of a morula into a blastocyst and to facilitate implantation. In further embodiments, the present invention provides for a second gestational proliferative agent, termed GPA-2, that has a molecular weight greater than 20,000 daltons. These proliferative agents, or embryonal explants comprising such agents, may be used in the treatment of infertility and/or hypoproliferative disorders.

4. DESCRIPTION OF THE FIGURES

FIG. 1. Results of HPLC analysis of the <8,000 MW fraction from spinal cord showing three dominant bands.

FIG. 2. Results of PAGE analysis of the <10,000 MW fraction from spinal cord.

FIG. 3. Superfusion apparatus.
1. GROWTH CHAMBERS containing the tissue being cultured.
2. TUBING SYSTEM: Silicone permitted the gas to get in the tubing system.
3. HEAT/GAS EXCHANGER which maintains the thermal environment in and around the growth chambers.
4. GAS TRANSFER is achieved by flooding the system with the desired gas.
5. INCOMING GAS (5% $CO_2$, 95% air).
6. ENTRANCE OF WARM WATER: (37° C.).
7. EXIT OF WATER after heating the exchanger.
8. ON: Starts the pump
9. MINIMUM: 0.01 ml/min
10. MAXIMUM 3 ml/min
11. DIRECTION: The direction of the lighted arrow indicates direction of fluid through the pump tubing.
12. FLOW RATE: From 00>99 represents a percentage of normal pumping rate.
13. AT THIS POINT, another peristaltic pump is added in order to add GnRH, or some other factors.
14. DIVISION of the principal tube.
15. MEDIUM RESERVOIR
16. PERISTALTIC PUMP.

FIG. 4A. Suppressive effect of the extract on secretion of hCG by placental explants. Efferent sample fractions were collected every 2.4 minutes and were sequentially numbered.

FIG. 4B. Suppressive effect of <8,000 MW fraction of extract on secretion of hCG by placental explants.

FIG. 4C. Sample identical to that of (4B) lost the ability to suppress hCG secretion after heat inactivation.

FIG. 5. Ability of various dilutions of total extract to suppress hCG secretion by placental explants. The following dilutions of extract in 0.05 M Tris-HCl PMSF-DTT (pH 7.4) were used: 1/20, 1/200, and 1/2000. Buffer alone was used as a control.

FIG. 6. Suppressive activity of the <8,000 MW fraction of extract on the proliferation of cancer cell lines. The number of cells in buffer-treated cultures serves as a control.

FIG. 7. Percent suppression of MCF-7 proliferation as a function of increasing dosage of <8,000 MW fraction protein.

FIG. 8A. Percentage of untreated control embryos attaining the morular stage.

FIG. 8B. Percentage of untreated control embryos exhibiting hatching/adhesion.

FIG. 9. The effect of various molecular weight fractions of extract on nude mice survival following inoculation with fibrosarcoma. Fraction 1 corresponds to MW <3,000; Fraction 2 corresponds to MW <30,000 MW; Fraction 3 corresponds to MW <8,000; Fraction 4 corresponds to MW <10,000; Fraction 5 corresponds to MW <100,000; and Fraction 6 corresponds to buffer-treated control.

FIG. 10. <3,000 MW fraction of embryo extract increased secretion of hCG by placental explants.

FIG. 11. Results of HPLC analysis of the <3,000 D molecular weight fraction associated with proliferative activity.

FIG. 12. Inhibitory effect of human embryonal brain fractions on MCF-7 cell proliferation separated using a Phase I HPLC Superdex 75 HR 10/30 column. Samples of 0.5 ml of the extract were applied and fractions of the 2 to 35 kDa region were recovered (0.5 ml/min) and tested on MCF-7 breast cancer cell proliferation. Inhibition was carried out by adding 2.5 µg/ml protein of the fraction of buffer alone for 4 d. Significant inhibitory effect was noted with the JDK-AP2 (~10.7 kDa) and JDK-AP1 (~4.5 kDa) region fractions, 40% and three-fold respectively (p<0.05), compared to buffer controls and 23–30 kDa region (fractions 21–23).

FIG. 13 (A and B) Inhibitory effect of human embryonal spinal cord JDK-AP1 (~4.5 kDa) and JDK-AP2 (~10.7 kDa) fractions on cell proliferation. The fractions were recovered as described in FIG. 12 and tested. Significant inhibition was obtained with the 4 cell lines tested compared to buffer controls. Maximal effect (70% reduction) was noted with JDK-AP2 (~10.7 kDa) on MCF-7 CELLS (C) The 23–30 kDa region fractions affected only the Balb/c 3T3 transformed fibroblast cell line. *=p<0.05.

FIG. 14. Phase I HPLC profile of porcine embryonal brain. Conditions were similar to those described in FIG. 12.

FIG. 15. Inhibition profile of MCF-7 cell proliferation following the addition of the fraction recovered following HPLC (FIG. 14). Significant inhibition was noted in the JDK-AP2 (~10.7 kDa) and JDK-AP1 (~4.5 kDa) regions.

FIGS. 16A–C. The gestational age-dependent inhibitory effect of porcine JDK-AP on MCF-7 breast cancer cell proliferation. Tissue extracts (brain and spinal cord) from the 40- and 70-day gestational periods were separated by HPLC (see FIG. 12) and tested. (A and B) The effect of JDK-AP1 (~4.5 kDa) and JDK-AP2 (~10.7 kDa) was significant while, (C) the 23–30 kDa region fractions had no significant effect on cell proliferation. The inhibitory effect of JDK-AP1 (~4.5kDa) was not evident in the early spinal cord. *=p<0.05.

FIG. 17. Dose-dependent inhibitory effect of the porcine-origin JDK-AP2 (~10.7 kDa) on MCF-7 cell proliferation. JDK-AP2 (~10.7 kDa) was concentrated, the buffer removed, and the concentrated sample was resuspended in DMEM and diluted. A significant inhibitory effect was noted at the 0.5 $\mu$/ml concentration, while maximal inhibition (58%) was obtained at 5 $\mu$g/ml.

FIG. 18. Time-dependent inhibitory effect of JDK-AP on MCF-7 cell proliferation. Maximal effects were noted after 5 d.

FIG. 19. SDS-PAGE (20%) of porcine-origin JDK-AP. Lanes 1, 2 and 3 show 150 $\mu$g/ml, 100 $\mu$g/ml and 50 $\mu$g/ml, respectively, of the total porcine brain. Lane 4 shows the Phase I (FIG. 14) HPLC-separated bioactive region of JDK-AP2 (~10.7 kDa). A number of bands were identified in the <35 kDa region. Lane 5 represents the MW standards run in parallel.

FIG. 20. Phase II HPLC profile (ion exchange) TSK-DEAE column of JDK-AP2 separation. The 1.5 ml fractions were collected and tested on MCF-7 cell proliferation.

FIG. 21A. Significant inhibitory effect of fraction 16 collected from Phase II HPLC (see FIG. 20) on proliferation of MCF-7 cells after 4 d.

FIG. 21B. SDS-PAGE gel analysis of the recovered fractions. Note the low protein content of the active fraction (see arrow).

FIG. 22. Phase III HPLC (preparative scale reverse phase) separation profile by Vidac C-4 column of the active fraction from Phase II HPLC. Samples were collected and tested. The antiproliferative effect was noted only with one peak (see arrow).

FIG. 23. Significant inhibitory effect of Phase III HPLC-separated fractions on proliferation of MCF-7 cells after 4 d compared to controls.

FIG. 24. 10% SDS-PAGE gel profile of the fractions separated by Phase III HPLC (FIG. 23). Only a couple of unique protein bands can be noted in lanes 12, 13, and 14 when compared to the inactive fractions (see arrow).

FIG. 25. Total separation of the proteins in the active fraction obtained following Phase IV reverse phase HPLC by using a phenyl column. A total of 2 major and 7 minor peaks were noted.

FIG. 26. Inhibitory activity of the fractions generated by phenyl reverse phase HPLC in FIG. 25 on MCF-7 proliferation after 4 d. Compared to blank, there was a significant inhibition (50%) in the 9 to 12 fractions. Note the low protein content of the sample in that region.

FIGS. 27A–D. Micro-photographs of the inhibitory effect of human JDK-AP2 (~10.7 kDa) on MCF-7 cell proliferation after 4 d. A significant reduction (70%) in cell number was noted. (A and C) Control (buffer treated) dishes at ×100 and ×200 magnifications, respectively. (B and D) ×100and ×200 magnifications of the cells following addition of JDK-AP2. Compared to controls, the cells following culture remained viable and attached to the dish, tended not to aggregate, and had a stellate or fusiform appearance in many cases.

FIG. 28. Inactivation of JDK-AP2 (~10.7 kDa) by heating and incubation with proteinase K. MCF-7 cells were cultured under each of these treatment conditions for 4 d. In each case, treatment abolished the effect compared to the active fraction as measured by [$^3$H]-thymidine incorporation. Lane 2, active fraction; Lane 3, heat inactivation; Lane 4, proteinase K.

FIG. 29. The effects of embryonal extract purified by TSK column chromatography on MCF-7 cell proliferation.

5. DETAILED DESCRIPTION OF THE INVENTION

The present invention provides for gestational agents that may be used to control cell proliferation. It is based, at least in part, on the theory that pregnancy operates, figuratively speaking, like a reversible cancer. The products of conception, similar to cancer, are invasive, penetrate the circulation and metastasize, express similar surface antigens, and secrete certain cancer-related compounds, such as alphafetoprotein and carcinoembryonic antigen. Furthermore, the conceptus, like a tumor, is not rejected by the body, but rather harnesses maternal resources to secure its well-being. Unlike cancer, however, the invasiveness and tolerance associated with pregnancy are reversible at almost any time.

The present invention relates to agents that operate to control the development of the embryo such that proliferation, invasiveness, and differentiation may occur without substantially injuring the maternal host. It has been discovered that several agents produced by the embryo appear to play an important role in its development. For example, as shown by FIG. 29, embryonal extract which has been fractionated by TSK column chromatography (see Section 9, infra) demonstrates the presence of multiple proliferative and antiproliferative factors. The various embodiments of the invention relate to such agents, and their use, for example, in the treatment of cancer and infertility, or for preventing pregnancy.

For purposes of clarity of description and not by way of limitation, the detailed description of the invention is divided into the following subsections:

(i) gestational antiproliferative agents;

(ii) gestational proliferative agents;

(iii) antibodies of the invention;

(iv) the use of gestational antiproliferative agents in cancer therapy;

(v) the use of gestational agents in controlling fertility; and (vi) additional utilities of the invention.

5.1. GESTATIONAL ANTIPROLIFERATIVE AGENTS

The present invention provides for mammalian gestational antiproliferative agents which are comprised in a class of proteins termed JDK-AP, which normally are produced by the mammalian embryo at a stage of development when chorionic gonadotrophin levels reach a plateau.

JDK-AP proteins may be prepared from any suitable mammalian embryo. As the size of the embryo will affect the ease with which individual organs are identified and isolated, it is desirable that the embryo be obtained from a relatively large mammal, such as, for example, but not by way of limitation, a human, non-human primate, horse, cow, sheep, or pig, etc. If obtained from a human, the embryo may be obtained, after proper consent, from the products of an elective or spontaneous abortion. In view of availability and freedom of human pathogens, the preferred source of JDK-AP proteins is porcine embryos. Cross-species activity of JDK-AP proteins has been observed, although JDK-AP obtained from a particular species may exert somewhat greater antiproliferative activity on cancer cells obtained from the same species.

It is desirable further that the embryo be of a developmental stage in which rapid development is occurring or has just begun to taper off. For example, in humans, it may be desirable to utilize an embryo which is between six and nine weeks of gestation. For non-human animals, embryos at a stage comparable to weeks six through nine of human gestation may preferably be used. For porcine embryos, it is desirable that the size of the embryos be between 5 and 10 cm, reflecting a developmental stage between about 40 and 70 days of gestation.

Any organ of the embryo may be utilized. In preferred embodiments of the invention the brain and spinal cord, (i.e. neural elements) or adrenal gland are preferably used. Visceral organs, such as lung, liver, or kidney may also desirably be used.

The present invention, in one specific, nonlimiting embodiment, provides for embryonal extracts comprising substantially purified JDK-AP proteins prepared by the following method, which is exemplified in Section 6, infra. The term "substantially purified", as used herein, refers to proteins which have been purified at least 15-fold, preferably more than 1,000 fold, and most preferably at least 10,000-fold relative to solubilized embryonal tissue. Embryonal tissue may be minced and placed in cold Tris-HCl at pH 7.4 containing 10 mM dithiothreitol (DTT) and 2 mM phenyl-methyl-sulfonyl-fluoride (PMSF), then sonicated on ice for about 60 seconds and then centrifuged at about 2400 rpm for about ten minutes to remove cellular debris. An initial amount of embryonal tissue weighing about 50 mg may, for example, be processed in about 1 ml of buffer and may yield about 1 ml of supernatant. The supernatant from the centrifuged material may then be separated into fractions based on molecular weight, using, for example, the Filtron System Omega Cell (Biolab), 30 mm diameter, under nitrogen, and the fractions containing molecular weights less than about 10,000 daltons may desirably be obtained. This fraction may, preferably, be further purified by polyacrylamide gel electrophoresis (PAGE). That portion of the resulting gel corresponding to molecular weights between about 3,000 and 8,000 daltons may then be separated from the rest of the gel and eluted to produce a partially purified embryonal extract comprising JDK-AP protein. Alternatively, the fraction may be further purified by HPLC as described in Section 6.1.3., infra, in which case three major peaks may be expected to be produced, as set forth in FIG. 1. The fractions corresponding to any or all of these three peaks may be collected to yield an embryonal extract which comprises substantially purified JDK-AP protein.

In other specific, nonlimiting aspects of the invention, two particular species of JDK-AP protein, termed JDKAP1 and JDK-AP2, have been substantially purified from human and pig embryos. JDK-AP1 has an apparent molecular weight of about 4.5 kd, within a range of 3.5–5 kd. JDK-AP2 has an apparent molecular weight of about 10.7 kd (within a range of 9.5–11.5) when isolated from human embryos and about 10–15 kd (preferably 10–12kd) when isolated from porcine embryos. The present invention is not to be limited to JDK-AP1 and JDK-AP2 originating in human and pig, and includes corresponding proteins prepared from other species of mammalian embryos which cross-react with antibodies directed toward JDK-AP1 or JDK-AP2, or which have an amino acid sequence which is at least about 70 percent homologous.

Accordingly, the present invention, in specific, nonlimiting embodiments, provides for embryonal extracts comprising substantially purified JDK-AP1 or JDK-AP2 proteins prepared by the following method, which is exemplified in Section 9, infra.

Porcine embryos (5 to 10 cm, corresponding to 40 to 70 days of gestation) may be immediately placed on ice after sacrifice and subsequently transferred to the laboratory for processing. The brain and spinal cord tissues may be dissected out on ice using microsurgical techniques. Tissue may be extracted and sonicated in 0.2 M Tris buffer 1 mM of PMSF and 2 mM of DTT (pH 7.4), centrifuged at 20,000 rpm. The supernatant may be filtered through 0.2 μm filters, and subjected to the following chromatographic methods. As a first phase of purification, the samples may be subjected to chromatographic filtration (based on molecular size). The samples may be applied to an HPLC column (Superdex 75 HR 10/30, LKB, Pharmacia, Piscataway, N.J.) which was previously equilibrated with the same buffer. Samples of 0.5 ml may be collected at a flow rate of 0.5 ml/min and frozen at −70° C. until used. This procedure may be scaled up using a TSK HW55 16/570 mm column, and 3 ml batch samples may be applied. The molecular weight of the various fractions may be estimated from the retention time of proteins with known molecular weight. Their protein content may be estimated by their absorbance at 280 nm. The active fractions may be concentrated using a Microsep (Filtron, Northborough, Mass.) with a <3 kDa cut-off filter. The concentrated samples may then be subjected to a second phase of HPLC (based on protein charge). The concentrated sample may be applied to an ion exchange column TSK-DEAE [Merck Fractogel 650 (M) 160/90 mm] which was equilibrated with 0.1 M Tris buffer containing 308 mg DTT/L at pH 7. The gradient flow may be 1.5 ml/min, and 1.5 ml fractions may be collected and tested. These fractions may then be subjected to a third phase of purification, reverse phase HPLC (based on protein hydrophobicity), using, for example, a C18 preparative column (Vydac). Samples may be run in a 0.1% TFA acetonitrile buffer, and fractions may be collected every minute. Recovered samples may be twice evaporated and resuspended in water. These samples may then be subjected to a fourth phase of purification, reverse phase phenyl HPLC, as follows. The active fraction resulting from the previous step may be applied to a phenyl reverse phase C-4 column, and samples of 1 ml/min may be collected and tested for antiproliferative activity. The resulting active fractions comprise substantially purified JDK-AP protein. Such fractions may be further purified by PAGE or IEF.

The JDK-AP proteins of the invention may also be prepared by any other method known in the art, including, but not limited to, chemical synthesis or recombinant DNA technology. Furthermore, the present invention provides for the preparation and use of fragments or derivatives of JDK-AP proteins, including fragments produced chemically, by recombinant DNA, or by protease activity, and derivatives obtained by, for example, glycosylation, phosphorylation, dephosphorylation or chemical conjugation of any compound to JDK-AP or a fragment thereof. Further, at least a portion of a JDK-AP protein may be sequenced, and the amino acid sequence so obtained may be used to deduce oligonucleotide probes that may be used directly to screen recombinant DNA libraries, or in polymerase chain reaction, in order to obtain JDK-AP encoding nucleic acid sequences. These sequences may then be inserted into an appropriate expression vector system and then may be expressed in quantity using standard techniques. Alternatively, JDK-AP proteins may be produced by chemical synthesis or by any other method known in the art.

5.2. GESTATIONAL PROLIFERATIVE AGENTS

The present invention provides for a class of gestational proliferative agents, termed JDK-P. One specific, nonlimiting embodiment of the invention is a specific protein termed GPA-1 that is comprised in an embryonal tissue extract and that has a molecular weight less than about 3,000 daltons and preferably about 1,500–2,000 D. The source of suitable embryonal tissue is as described in Section 5.1., supra, except that embryos at a developmental stage comparable to six weeks of human gestation may also be used.

GPA-1 may be prepared as follows according to a specific, nonlimiting embodiment of the present invention. Embryonal tissue may be minced and placed in cold Tris-HCl at pH 7.4 containing 10 mM dithiothreitol (DTT) and 2 mM phenyl-methyl-sulfonyl-fluoride (PMSF), then sonicated on ice for about 60 seconds, and then centrifuged at about 2400 rpm for about ten minutes to remove cellular debris. An initial amount of embryonal tissue weighing about 50 mg may, for example, be processed in about 1 ml of buffer and may yield about 1 ml of supernatant. The supernatant from the centrifuged material may then be separated into fractions based on molecular weight, using, for example, the Filtron System Omega Cell (Biolab), 30 mm diameter, under nitrogen and the fraction containing molecular weights less than 3,000 D may desirably be obtained. This fraction may, preferably, be further purified by polyacrylamide gel electrophoresis. That portion of the gel corresponding to a molecular weight less than about 3,000 D may then be separated from the rest of the gel and eluted to form the gestational proliferative agent GPA-1. See Section 8, infra.

Accordingly, the present invention provides for a substantially purified protein, GPA-1, having a molecular weight of less than about 3,000 daltons that is expressed in mammalian embryonal tissue and that has a proliferative effect on morular cells. In preferred embodiments, this protein has a molecular weight greater than 1,400 D, and in most preferred embodiments, the molecular weight is about 2,000 D. GPA-1 also is capable of increasing the secretion of hCG by placental explants, of promoting the development of a morula into a blastocyst, and of facilitating implantation.

The present invention further provides for a second gestational proliferative agent termed GPA-2 that has a molecular weight above 20,000.

5.3 ANTIBODIES OF THE INVENTION

According to the invention, gestational proliferative agents (i.e. JDK-P proteins such as GPA-1 and GPA-2) and gestational antiproliferative agents (i.e. JDK-AP proteins) or active fragments or derivatives thereof, may be used as immunogens to generate antibodies.

To improve the likelihood of producing an immune response, the amino acid sequence of the gestational agent may be analyzed in order to identify portions of the molecule which may be associated with increased immunogenicity. For example, the amino acid sequence may be subjected to computer analysis to identify surface epitopes. Alternatively, the deduced amino acid sequences of gestational agent from different species could be compared, and relatively non-homologous regions identified; these non-homologous regions would be more likely to be immunogenic across various species.

For preparation of monoclonal antibodies directed toward the antigens of the invention, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the antigens of the invention. For the production of antibody, various host animals can be immunized by injection with antigen, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, PLURONIC polyols, polyanions, peptides, oil emulsions, keyhole limpet hemocyanins, dinitrophenol, and potentially useful human adjuvants such as BCG (Bacille Calmette-Guerin) and, *Corynebacterium Darvum.*

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with papain and a reducing agent.

5.4. THE USE OF GESTATIONAL AGENTS IN CANCER THERAPY

The present invention provides for a method of inhibiting the proliferation of cancer cells comprising exposing said cells to an effective concentration of gestational antiproliferative agent (i.e. a JDK-AP protein). In preferred embodiments of the invention, the gestational antiproliferative agent is comprised in an embryonal extract or is a substantially purified protein such as JDK-AP1 or JDK-AP2 as described in Section 5.1., supra.

The present invention provides for a method of treating a patient suffering from cancer comprising administering to the patient an effective amount of said gestational antiproliferative agent in a suitable pharmaceutical carrier.

The present invention may be used to inhibit proliferation of a wide variety of cancer cells and to treat a wide variety of cancers. As exemplified in Section 7, infra, embryonal extract comprising substantially purified JDK-AP protein was observed to inhibit the proliferation of all cancer cell lines tested, suggesting that it has a broad spectrum of activity both in vitro and in vivo. Further, as exemplified in Section 9, infra, the substantially purified proteins JDK-AP1 and JDK-AP2 were observed to inhibit proliferation of cancer cells. JDK-AP1 was found to inhibit the proliferation of a wide variety of cancer cell lines, while not significantly inhibiting the proliferation of nonmalignant cells. Accordingly, the present invention may be used to inhibit proliferation of cancer cells arising from any tissue, including, but not limited to breast, bone marrow, lymphoreticular system, ovary, kidney, lung, brain, intestine, stomach, esophagus, pancreas, spinal cord, mucosa, germ cell, bone, muscle, skin (e.g. melanoma) etc. The present invention may be used to treat cancer arising from any tissue in a patient, including, but not limited to, cancer of the breast, ovary, kidney,lung,brain, intestine, bone marrow, lymphoreticular system, stomach, esophagus, pancreas, spinal cord, mucosa, germ cell, bone, muscle, skin (e.g. melanoma), choriocarcinoma, etc.

An effective concentration of gestational antiproliferative agent may be defined as any concentration that is capable of inhibiting the proliferation of MCF-7 cells,under conditions as set forth in Section 7, infra, by at least 10 percent relative to untreated control. An effective amount of gestational antiproliferative agent to be used in patient treatment may be defined as that amount that produces an effective concentration of gestational antiproliferative agent in the tissue of interest.

In methods of treatment according to the invention, gestational antiproliferative agent may be administered by any route known in the art, including, but not limited to, intravenous, subcutaneous, intramuscular, by injection into a tumor or by other local injection, intranasal, intraocular, intraperitoneal, oral, etc. Further, gestational antiproliferative agent may be coupled to another molecule, such as an antibody, or to a magnetic bead in order to target delivery, or may be administered via a solid or semisolid implant, such as a sustained-release implant. Gestational antiproliferative agent may be incorporated into microcapsules, microspheres, or liposomes. Further, gestational antiproliferative agent may be coupled to another molecule, such as an antibody, or to a magnetic bead in order to target delivery. If orally administered, it may be desirable to provide a means to protect the gestational antiproliferative agent from denaturation in the stomach.

A suitable pharmaceutical carrier, according to the invention, is any vehicle which is relatively nontoxic to humans and which preserves the activity of the gestational antiproliferative agent. Suitable carriers include, but are not limited to, water, saline, phosphate buffered saline, dextrose, etc.

5.5. THE USE OF GESTATIONAL AGENTS IN CONTROLLING FERTILITY

According to the invention, a gestational antiproliferative agent (i.e. a JDK-AP protein) may be used to prevent pregnancy, and gestational proliferative agents (i.e. a JDK-P protein such as GPA-1 and/or GPA-2) may be used to enhance fertility and to protect early pregnancy.

The present invention provides for a method of preventing pregnancy (in which development and/or implantation of the embryo is prevented) comprising administering to a female subject an effective amount of a gestational antiproliferative agent in a suitable pharmaceutical carrier. In preferred embodiments of the invention, the gestational antiproliferative agent is an embryonal extract or is a substantially purified protein such as JDK-AP1 or JDK-AP2 as described in Section 5.1., supra.

The present invention further provides for a method of improving the fertility of a subject comprising administering to the subject an effective amount of gestational proliferative agent (i.e., a JDK-P protein such as GPA-1 and/or GPA-2) in a suitable pharmaceutical carrier. In preferred embodiments of the invention, the gestational proliferative agent(s) is (are) a substantially purified protein(s).

A subject is any human or non-human mammalian subject. The fertility promoting aspect of the invention may be particularly useful in improving the fertility of livestock.

An effective amount of gestational antiproliferative agent is construed, in embodiments relating to the prevention of pregnancy, to refer to an amount that will result in a concentration in at least a portion of the reproductive organs of the subject that is the same as a concentration that will inhibit morular development of mouse embryos, under conditions as described in Section 7.1.3., by at least about 50 percent relative to untreated controls.

An effective amount of gestational proliferative agent is construed, in embodiments relating to fertility, to refer to an amount that will result in a concentration in at least a portion of the reproductive organs of the subject that is the same as a concentration that will increase the number of morula that progress to form blastocysts by at least 50 percent relative to untreated controls under conditions as described in Section 8, infra.

The fertility-controlling agents may be administered by any method known in the art, as described in Section 5.4., supra.

Suitable pharmaceutical carriers that may be used according to the invention are relatively nontoxic to the host and preserve the activity of the agent, and include those set forth in Section 5.4., supra.

In further embodiments of the invention antibody directed toward gestational proliferative agent (i.e. GPA-1 and/or GPA-2) may be used in methods of preventing pregnancy. The present invention provides for a method of preventing pregnancy comprising administering to a female subject an effective amount of antibody that binds to a gestational proliferative agent. In alternative embodiments, the present invention provides for a method of preventing pregnancy comprising immunizing a female subject with an immunogenic preparation comprising a gestational proliferative agent. Such an immunogenic composition may comprise an adjuvant, such as Freund's complete adjuvant, and may desirably comprise gestational proliferative agent coupled to an immunogenic compound or a gestational proliferative agent obtained from a species that is different from the subject to be immunized. Of note, such immunization may result in irreversible prevention of pregnancy.

5.6. ADDITIONAL UTILITIES OF THE INVENTION

In additional embodiments of the invention, gestational antiproliferative agent may be used in the treatment of disorders of increased cell proliferation including, but not limited to, premalignant conditions, keloids, Von Recklinghausen disease, familial polyposis, benign neoplasms (e.g. breast adenomas), autoimmune diseases such as rheumatoid arthritis, etc. Such agents may also be used prophylactically in subjects who are at risk for developing neoplasms, such as cancer.

In still further embodiments of the invention, a gestational proliferative agent (i.e. GPA-1 and/or GPA-2) may be used in the treatment of disorders of decreased cell proliferation, such as burnt-out myeloproliferative disorders, pernicious anemia, Sjogren's syndrome, etc. Gestational proliferative agent(s) may also be used to treat conditions in which increased cell proliferation is desirable, for example, to replace cells damaged by infarct, infection, injury, or exposure to a toxic agent (e.g. post-myocardial infarction myocardium, nervous system tissue that has been damaged or lost by infarction, infection, injury or exposure to toxic agent bone marrow that has been damaged by disease or by exposure to a toxic agent, skin that has been damaged or lost, e.g. in burn patients). In a specific, nonlimiting embodiment of the invention, gestational proliferative agent(s) may be used to promote liver regeneration. In another specific, nonlimiting embodiment of the invention, gestational proliferative agent(s) may be used to facilitate the incorporation of grafted tissue into a subject. In other specific, nonlimiting embodiments of the invention, gestational proliferative agent(s) may be used to promote wound healing and/or hair growth.

In additional embodiments, the levels of JDK-AP protein in a serum sample from a pregnant subject may be used to evaluate the likelihood that the pregnancy will proceed to term. For example, if, during weeks 7–10 of human gestation, the levels of JDK-AP protein in a human female subject were found to be higher than the levels of JDK-AP proteins in a control subject (also at the same stage of gestation, in a normal healthy pregnancy), there may be an increased likelihood of pregnancy failure. The levels of JDK-AP protein may be measured either by testing the antiproliferative activity of a <10,000 MW fraction of the serum sample, or by preparing antibodies to substantially purified JDK-AP proteins (or to embryonal extracts comprising such proteins) and then using such proteins to measure the amount of JDK-AP protein present in the serum.

The gestational agents of the invention may be utilized in vivo or in vitro.

For example and not by way of limitation, GPA-1 and/or GPA-2 may be used to promote the growth of cells or tissue in culture.

As a further example, gestational antiproliferative agents may be used in methods for determining whether a sample of tissue is premalignant or malignant. Cell cultures prepared from (1) a sample of normal tissue ("control culture") and (2) a sample of tissue to be tested for the presence of a malignancy ("test culture") may each be exposed to one or more concentrations of a JDK-AP protein or an embryonal extract comprising such protein(s). The ability of the protein or extract to inhibit the proliferation of cells in the test culture relative to the control culture may bear positive correlation to the presence of malignant cells in the test culture.

6. EXAMPLE: PREPARATION OF EMBRYONAL EXTRACTS CONTAINING SUBSTANTIALLY PURIFIED JDK-AP PROTEINS

6.1. MATERIALS AND METHODS

6.1.1. EXTRACTION

Human embryos of up to 9 weeks, which were the products of terminated pregnancy and obtained with permission, were isolated from the other products of conception aseptically, and gestational ages were confirmed by last menstrual period and crown-rump measurement of the specimen, with an experimental error of ±3 days. Embryonal organs were dissected from the embryo and identified using a dissecting microscope, and were placed on ice. All subsequent steps were carried out at 4° C.

Visceral organs comprising lung, liver, kidney and adrenal, and/or neural organs such as spinal cord and brain, were extracted by sonication on ice followed by centrifugation (2,400 rpm×10 min.) in 0.5 M Tris-HCl buffer at pH 7.4, dithiothreitol (DTT) 10 mM and phenyl-methylsulphonyl-fluoride (PMSF) 2 mM. Extraction with ethanol resulted in an approximately 3-fold lower activity product.

6.1.2. PREPARATION OF DIFFERENT MOLECULAR WEIGHT FRACTIONS

Using the Filtron System Omega Cell (Biolab Labs, 30 mm diameter), under nitrogen, the extract obtained according to (A) above from embryonic spinal cord was filtered through different molecular weight (M.W.) filters using the PBS buffer with DTT and PMSF. Each 1 ml of extract was filtered with 30 ml of buffer. The collected extract was lyophilized and the sediment was suspended in distilled water and stored at −20° C.

The following fractions were prepared (the symbol "<" being used, as conventional, to indicate fractions having "less than" the indicated M.W.): <100,000, <30,000, <10,000, <8,000 and <3,000. All fractions were tested for the ability to modulate HCG production of placental explants by using the superfusion model described by Barnea and Kaplan (1989, J. Clin. Endocrinol. Metab. 69:215–217) (see Section 7, infra). Only fractions below about 10,000 were found to be biologically active.

6.1.3. HIGH PRESSURE LIQUID CHROMATOGRAPHY ANALYSIS

High pressure liquid chromatography (HPLC) analysis was performed on the <8,000 MW fraction of spinal cord extract using a Hitachi HPLC apparatus and a 25 cm RP-18 column at 25° C. The sample was applied in water and eluted using 40 percent $H_2O$, 60 percent $CH_3OH$ (Volume/volume) at a flow rate of 1 ml/min.

Approximately 50 mg of tissue was sonicated in 0.5 ml of 0.2 M Tris buffer containing $10^{-3}$ M PMSF and 2 mM DTT pH 7.4, centrifuged at 20,000 rpm and the supernatant was filtered through a 0.2 µm filter. A sample (335 µl of 16 mg protein/ml) was applied on a HPLC column (Superdex 75HR 10/30, LKB, Pharmacia) which was previously equilibrated with the same buffer. Samples of 0.5 ml were collected at a flow rate of 0.5 ml/min and frozen at −70° C. until used. The molecular weights of the various fractions were estimated from the retention time of proteins with known molecular weights.

6.1.4. POLYACRYLAMIDE GEL ELECTROPHORESIS ANALYSIS

Polyacrylamide gel electrophoresis (PAGE) was performed on the <10,000 MW fraction using a 12.5 percent gel. The resulting gel was then stained with Coomassie blue using standard techniques.

6.2. RESULTS AND DISCUSSION

Extracts of various embryonic organs, prepared as described above, were subjected to fractionation by molecular weight. Only extract fractions having a molecular weight less than 10,000 daltons were found to be capable of altering HCG production of placental explants.

When the <8,000 MW fraction was subjected to HPLC analysis, three peaks were visualized as shown in FIG. 1. Similarly, when the <10,000 MW fraction from spinal cord was subjected to PAGE, three dominant bands appeared at molecular weights of approximately 3,000 to 8,000 daltons, as shown in FIG. 2. The class of substantially purified proteins in these embryonal extracts, which have antiproliferative activity, is termed "JDK-AP" proteins. Further HPLC analysis indicated the presence of a particular JDK-AP protein having a molecular weight of about 6.43 KDA.

7. EXAMPLE: EMBRYONAL EXTRACTS CONTAINING JDK-AP PROTEINS HAD A SUPPRESSIVE EFFECT ON HCG SECRETION BY PLACENTAL EXPLANTS, AN ANTIPROLIFERATIVE EFFECT ON EMBRYONIC DEVELOPMENT

7.1 MATERIALS AND METHODS

7.1.1. ANALYSIS OF EXTRACT FRACTIONATED BY MOLECULAR WEIGHT FOR ABILITY TO SUPPRESS HCG SECRETION BY PLACENTAL EXPLANTS

In order to determine suppressive activity, a super-fusion apparatus (Accusyst, Endotronics, St. Paul, Minn.) (FIG. 3) with a multichannel peristaltic pump and fraction collector (model 272, ISCO, Durham, N.C.) was used to study the short term dynamics of human chorionic gonadotropin (hCG) secretion, as described in Barnea and Kaplan (1989, J. Clin. Endocrinol. 69:215–217). Placental explants (200–300 mg wet weight) were placed into the culture chambers and a 18 mM HEPES/DMEM solution was washed through it in an atmosphere of 5% $CO_2$ and 95% air at 37° C. Sample corresponding to a particular molecular weight fraction was applied by administering a one minute pulse such that all fractions could be analyzed in parallel. Experiments were conducted for a 120-minute period. A 1 ml sample from the effluent of the apparatus was collected every 2.4 minutes for hCG measurements by radioimmunoassay. In such experiments, one channel served as control and four served as experimental channels. At given intervals a 1-minute pulse of an aqueous solution of the tested fraction was given through a peristaltic pump equipped with a digital flowmeter (Ismatech DD, Chicago, Ill.). The fractions that caused a significant change in hCG secretion following administration of the pulses were considered as "active samples".

7.1.2. TESTING OF JDK-AP ACTIVITY ON CANCER CELL LINES

Cell lines for testing, obtained from the American Type Culture Collection, Rockville, Md., were MCF-7, a breast cell line (accession number: HTB22) and HBL-40, a breast cell line exposed to SV40 virus, (accession number: HTB124). Other cell lines used included CRL, a kidney cell line, and GNL, an ovarian cell line.

Cells were cultured in RPMI-1640 with 10–15% fetal calf serum at a concentration of 10,000 cells per milliliter in a volume of 0.5 ml, and kept at 37° C. in a 95 percent air/5 percent $CO_2$ atmosphere. 10–50 microliter aliquots of extract from <8,000 and <10,000 fractions, corresponding, respectively, to protein concentrations of 0.2–1.0 microgram per ml were added to identical cultures in order to evaluate the dose-response. Two control cultures were used for each cell line. The first was an untreated culture. The second control was a culture to which 50 microliters of Tris-HCl were added. Extract was added to cultures only at the beginning of the experiment. After 3–5 days, the number of cells was counted using an automatic cell counter.

7.1.3. ANALYSIS OF THE EFFECT OF JDK ON EMBRYONAL DEVELOPMENT IN VITRO

ICR-strain mice were obtained from Charles River Laboratory. Females (between six and seven weeks old) were mated with ten to twelve-week old males. About 72 hours later, the females were sacrificed and morula-stage embryos were removed by flushing out the fallopian tubes with HAM-F1. The embryos were then placed in EBSS medium containing 10 percent newborn cord serum maintained in a humidified, 95 percent air/5 percent $CO_2$ atmosphere. For trophoblast development studies, the culture dishes were pre-coated with a 1 mm thickness of collagen.

7.1.4 ANALYSIS OF THE EFFECT OF EXTRACT FRACTIONS ON THE SURVIVAL OF NUDE MICE INOCULATED WITH FIBROSARCOMA

Adult mice (Balb/c) were treated by sublethal irradiation with x-rays to destroy their ability to form an immunological response. Experiments were carried out in which mice were subcutaneously inoculated with 100,000 cells of a fibrosarcoma cell line. Five mice were used for each experiment, and five mice that were not inoculated served as controls. In addition, inoculated mice were treated by injecting 50 $\mu$l of about 1 $\mu$g/ml of protein-like material from different molecular weight fractions obtained as described supra immediately after tumor inoculation. Subsequently, the animals were kept in a germ free environment, fed ad libitum, and were examined weekly. After 3 weeks the mice were sacrificed and examined for the presence of tumors.

7.2. RESULTS AND DISCUSSION

7.2.1. EXTRACT FRACTIONS CONTAINING MOLECULES HAVING A MOLECULAR WEIGHT LESS THAN 10,000 DALTONS SUPPRESSED HCG SECRETION BY PLACENTAL EXPLANTS

When placental explants were exposed to fractions of embryo extract corresponding to molecular weights <100,000, <30,000, <10,000, <8,000, and <3,000 daltons, only those fractions representing molecular weights less than 10,000 daltons were observed to suppress hCG secretion. The <10,000 fraction appeared to exhibit lower suppressive activity than the <8,000 fraction, whereas the <3,000 fraction exhibited a stimulatory activity.

7.2.2. JDK-AP SUPPRESSED THE GROWTH OF CANCER CELL LINES IN VITRO

Figure 1:
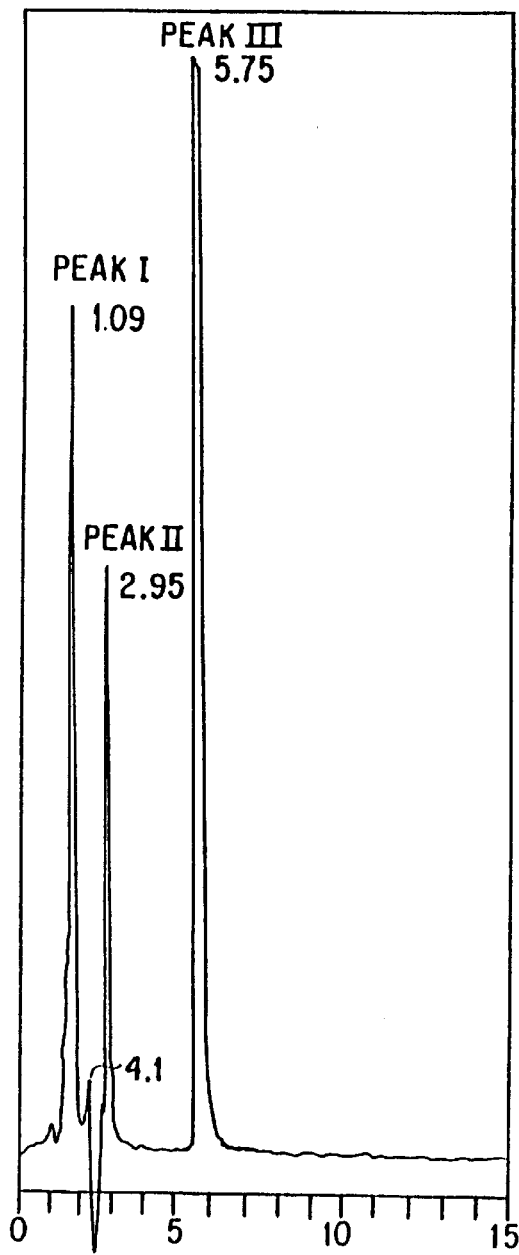

Fifty microliter aliquots of <8,000 MW and <10,000 molecular weight fractions of embryo extract were added to cell cultures of MCF-7, CRL, HBL-40, and GNL as described above and the number of cells in each treated culture was counted at the end of 3–5 days and compared to the number of cells in untreated control cultures (expressed as 100%) and cultures to which buffer had been added (buffer control).

As shown in Table I, infra, the cell count in MCF-7 cultures treated with the <8,000 MW fraction was 11 percent of control, representing an 89 percent inhibition of growth. In another experiment, after only three days of culture in the presence of a 6.428 KD molecular weight fraction of extract, cellular proliferation was inhibited by a statistically significant 10 percent ($p < 0.05$). Similarly treated cultures of (i)

CRL attained a cell count of 63 percent of control, representing 37 percent inhibition; (ii) HBL-40 attained a cell count of 3 percent of control, representing 97 percent inhibition; and (iii) GNL reached a cell count of 23 percent of control, representing 77 percent inhibition. Interestingly, the <10,000 MW fraction showed significant inhibition in only MCF-7 cultures. This may reflect the presence of some compound(s) that may limit the effect of the active fraction on the other cell lines.

TABLE I

| Cell Line | Percentage Of Untreated Control | | | |
|---|---|---|---|---|
| | Untreated Control | <8,000 MW | <10,000 MW | Buffer Control |
| MCF-7 | 100 | 11 | 50 | 97 |
| CRL | 100 | 63 | 100 | 100 |
| HBL-40 | 100 | 3 | 103 | 105 |
| GNL | 100 | 23 | 104 | 98 |

Figure 6:
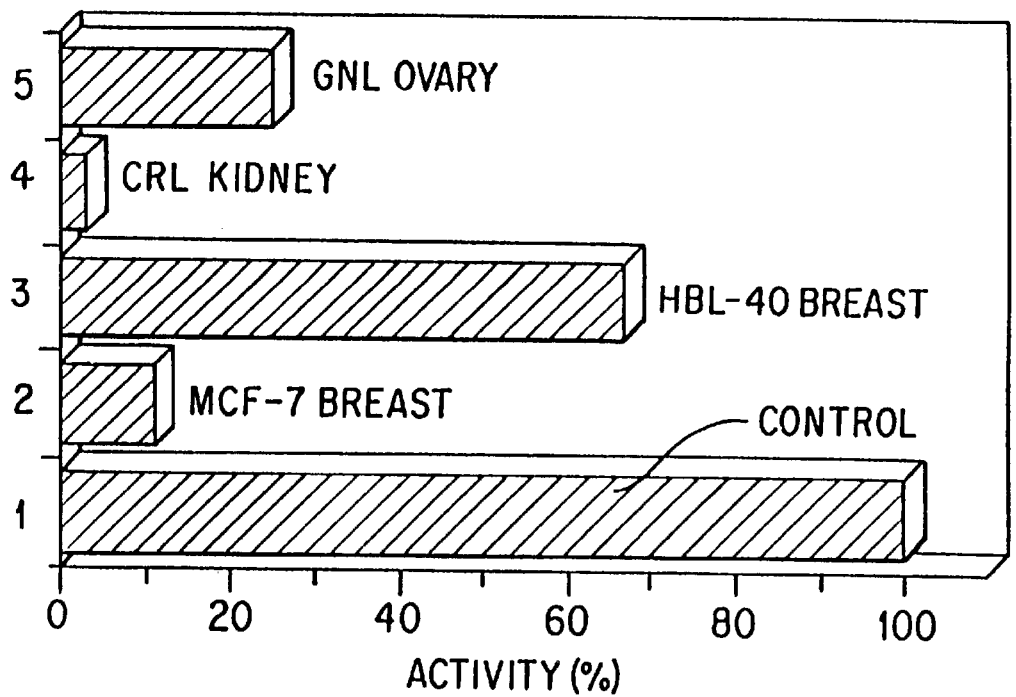

The results of another, similar experiment are presented in FIG. 6. In this experiment, extract had a more pronounced effect on CRL cells than in the experiment depicted in Table I; this may be a function of heterogeneity in the extract itself or of the proliferative state of the cells prior to each experiment.

Figure 7:
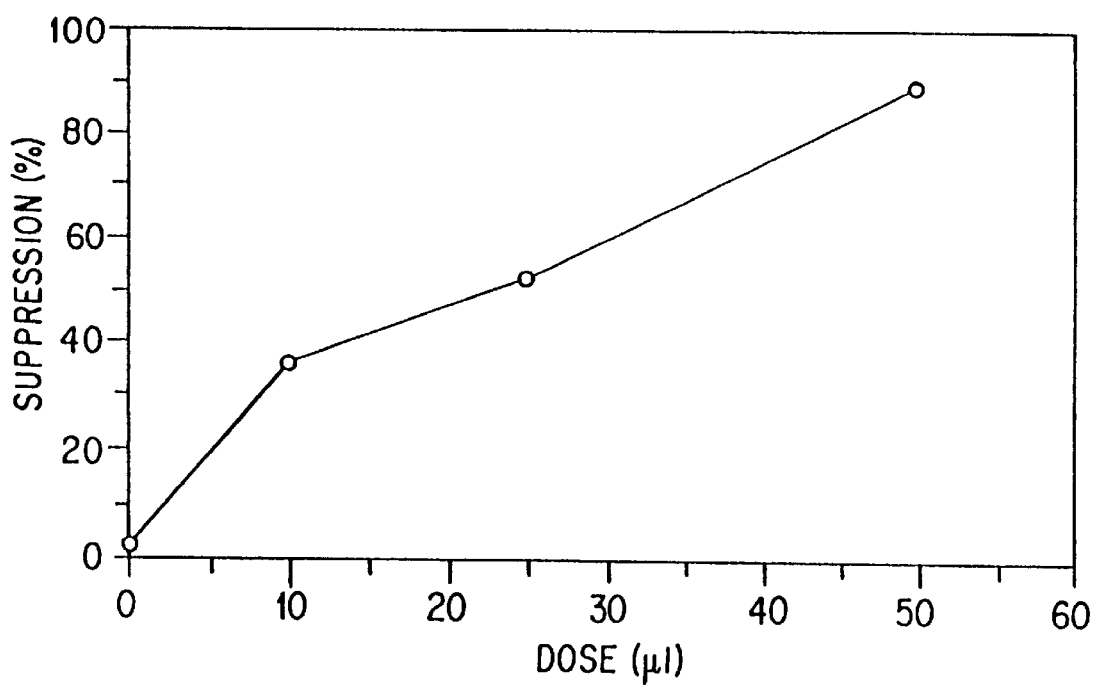
Figure 4B:
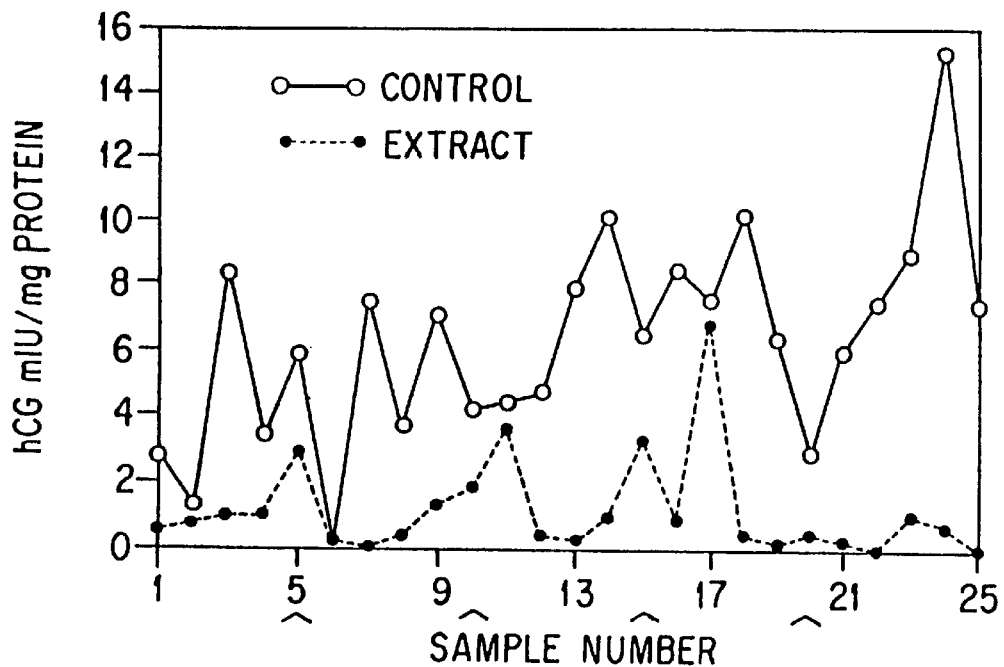
(FIG. 4C), indicating that JDK-AP activity is heat labile.
Figure 4C:
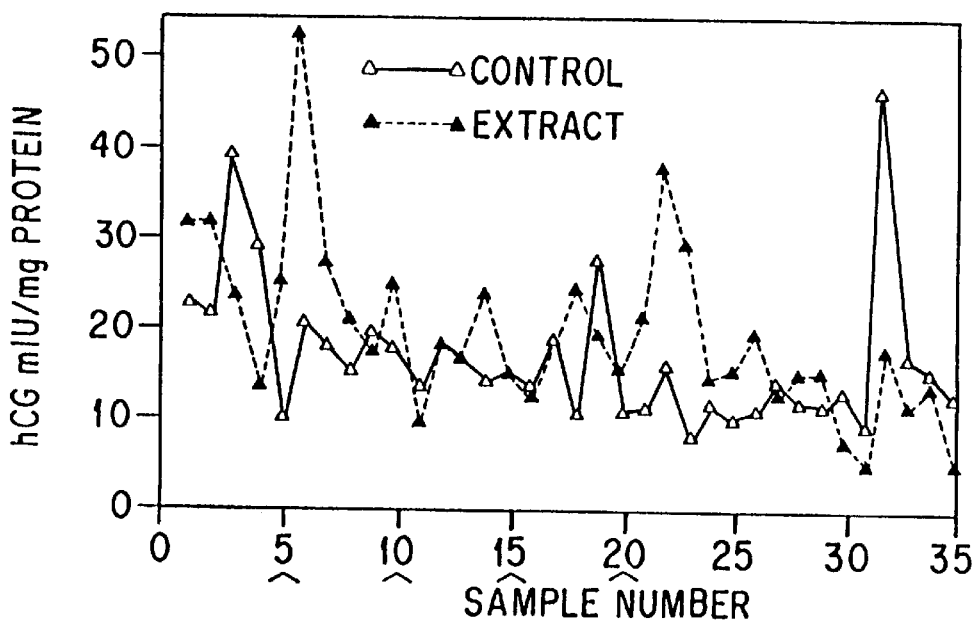
Figure 5:
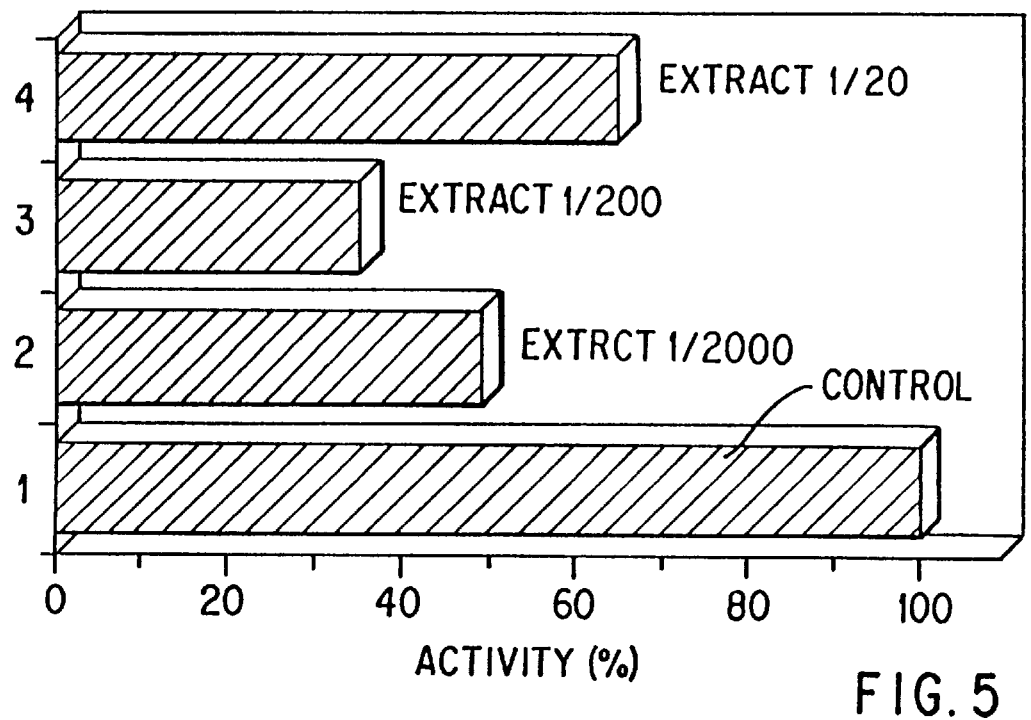
FIG. 5 illustrates that even a 1/2000 dilution of extract, corresponding to a protein concentration of about 100 ng/ml, was observed to achieve about 50 percent of the suppressive effect associated with control.

Table II, infra, and FIG. 7 illustrate the dose dependency of the antiproliferative effect of JDK in the <8,000 MW fraction on MCF-7 cells in culture. Cell count reduction became detectable when 10 $\mu$l of extract was used, corresponding to a protein concentration of 0.2 $\mu$g/ml. Maximal decrease was obtained with 50 $\mu$l of extract corresponding to 1.0 $\mu$g/ml of protein.

TABLE II

| Treatment | Percent Count Reduction |
|---|---|
| Untreated control | 0 |
| Buffer control | 3 |
| 10 $\mu$l <8,000 extract (0.2 $\mu$g/ml protein) | 36 |
| 25 $\mu$l <8,000 extract (0.5 $\mu$g/ml protein) | 52 |
| 50 $\mu$l <8,000 extract (1.0 $\mu$g/ml protein) | 89 |

7.2.3. SUPPRESSIVE EFFECT OF JDK IN EXTRACT ON EMBRYONAL DEVELOPMENT IN VITRO MOUSE

Figure 8A:
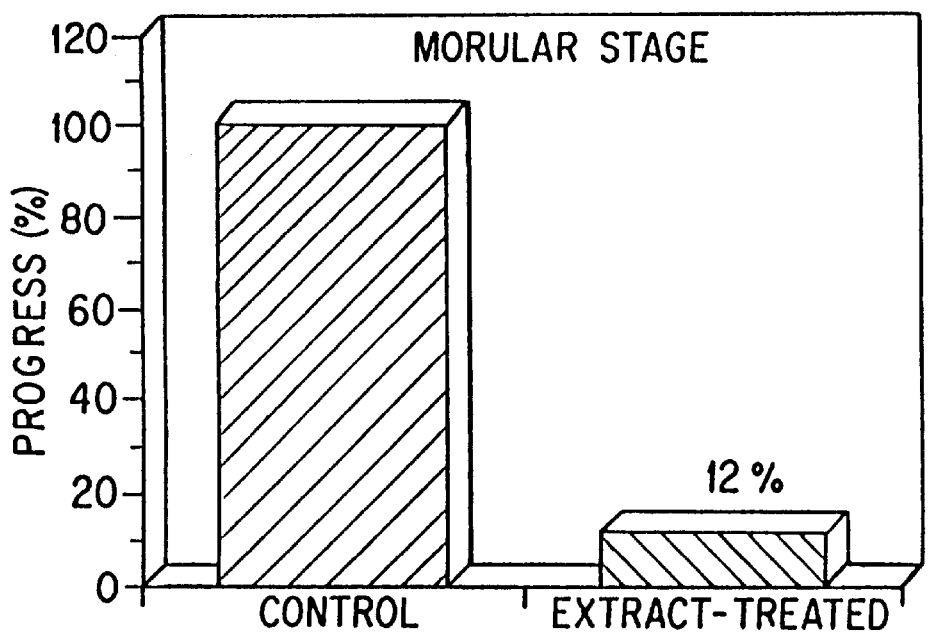
Figure 8B:
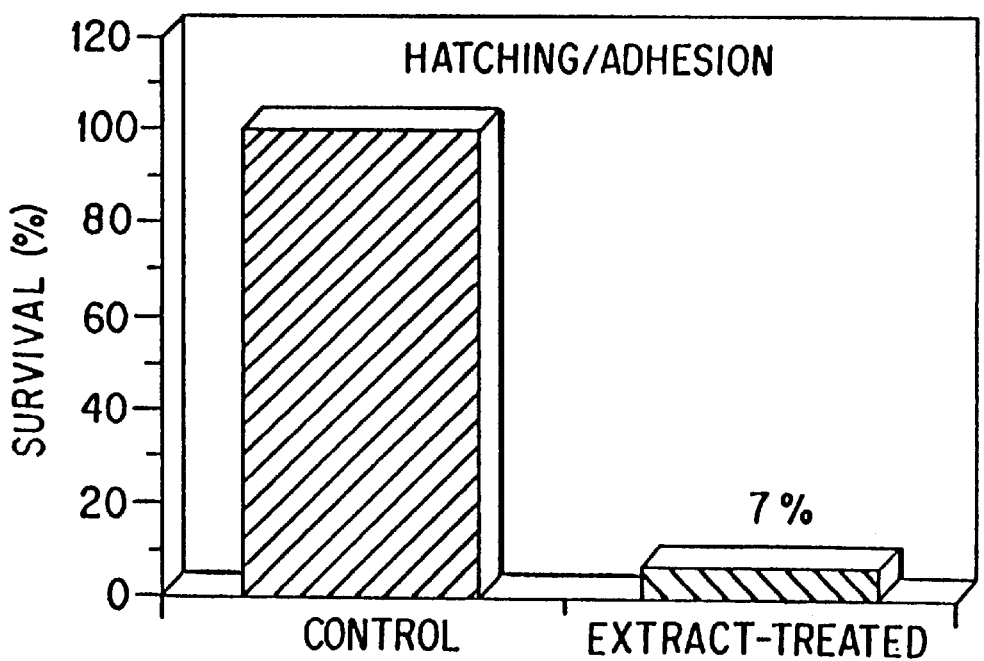
Figure 9:
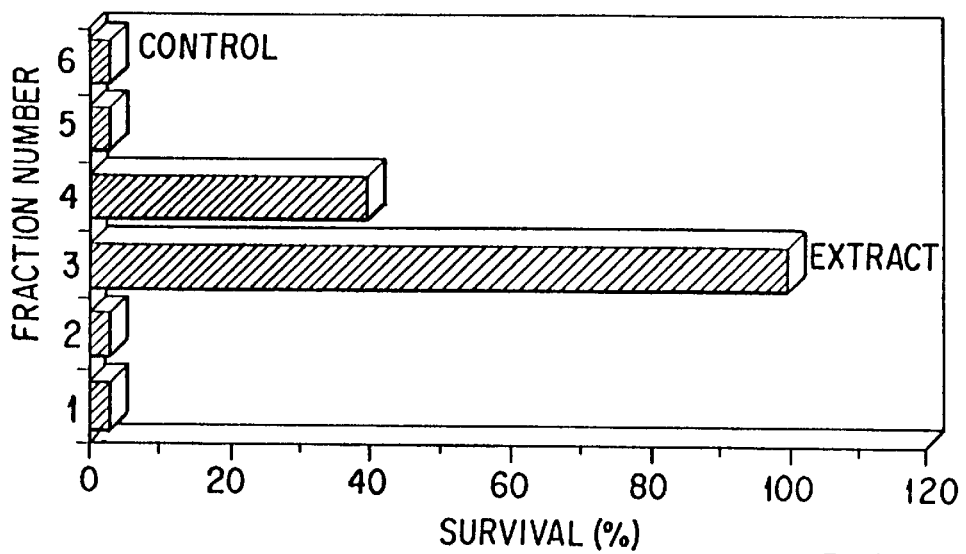

As shown in FIG. 8A and 8B mouse embryos treated with JDK in <8,000 MW fraction of extract did not develop normally, as compared to untreated control embryos. The number of extract-treated embryos which reached morular stage was observed to be only about twelve percent of untreated controls (FIG. 8A) and the number of extract-treated embryos which exhibited hatching/adhesion (measured by light microscopy) was only about seven percent of untreated controls (FIG. 8B). This is consistent with the antiproliferative activity of JDK and supports its use as a contraceptive agent.

7.2.4. JDK-TREATED NUDE MICE INOCULATED WITH FIBROSARCOMA SHOW IMPROVED SURVIVAL AND FEWER TUMORS

Thirty nude mice were inoculated with fibrosarcoma cells and divided into six groups of five mice each. Five uninoculated mice served as negative controls. One group of inoculated mice was treated only with Tris-HCl buffer. The remaining five groups were treated with 50 $\mu$l of about 1 $\mu$g/ml of one of the following extract fractions: <3,000 MW; <8,000 MW; <8,000 MW; <10,000 MW; and <30,000 MW.

As shown in Table III, all five mice in the group treated with the <8,000 MW fraction were tumor-free. The only other group that contained tumor-free animals was the group receiving the <8,000 molecular weight fraction (2 out of 5). Of the remaining groups, tumors were found to occur at the site of inoculation.

TABLE III

| Treatment | Tumor Free |
|---|---|
| None (control) | 5/5 |
| PBS Buffer | 0/5 |
| <3,000 | 0/5 |
| <8,000 | 5/5 |
| <8,000 | 2/5 |
| <10,000 | 0/5 |
| <30,000 | 0/5 |

In a similar experiment, the survival of mice inoculated with fibrosarcoma and then either untreated (control) or treated with various molecular weight fractions of extract was evaluated over a three week period. Survival was measured as the number of mice surviving after the three week period. The tumor-cell inoculated mice receiving fraction 3, corresponding to <8,000 MW fraction of extract, exhibited a survival equivalent to those of mice that had not been inoculated with tumor.

8. EXAMPLE: PREPARATION OF ACTIVE GESTATIONAL PROLIFERATIVE AGENTS 8.1. MATERIALS AND METHODS 8.1.1. PREPARATION OF GESTATIONAL PROLIFERATIVE AGENT-CONTAINING EXTRACTS

The <3,000 molecular weight fraction was obtained by mincing embryonal spinal cord in cold Tris-HCl at pH 7.4 containing 10 mM DTT and 2 mM PMSF, sonicating the minced tissue on ice for about 1 minute, and then centrifuging at about 2400 rpm for 10 minutes. The supernatant from the centrifuged material was then subjected to sizing using a Filtron System Omega Cell (Biolab) under nitrogen, and the fractions containing molecular weights less than 3,000 D were collected.

8.1.2. PREPARATION OF MOUSE EMBRYOS

ICR-strain mice were obtained from Charles River Laboratory. Females (between six and seven weeks old) were mated with ten to twelve-week old males. About 72 hours later, the females were sacrificed and morula-stage embryos were removed by flushing out the fallopian tubes with HAM-F1. The embryos were then placed in EBSS medium containing 10 percent newborn cord serum maintained in a humidified, 95 percent AIR/5 percent $CO_2$ atmosphere. For trophoblast development studies, the culture dishes were pre-coated with a 1 mm thickness of collagen.

8.1.3. ANALYSIS OF EFFECT OF EXTRACT ON HCG SECRETION BY PLACENTAL EXPLANTS

The effect of the <3,000 MW extract on hCG secretion by placental explants was evaluated using a superfusion apparatus as set forth in Section 7.1.1., supra.

8.1.4. HIGH PERFORMANCE LIQUID CHROMATOGRAPHY ANALYSIS

Figure 11:
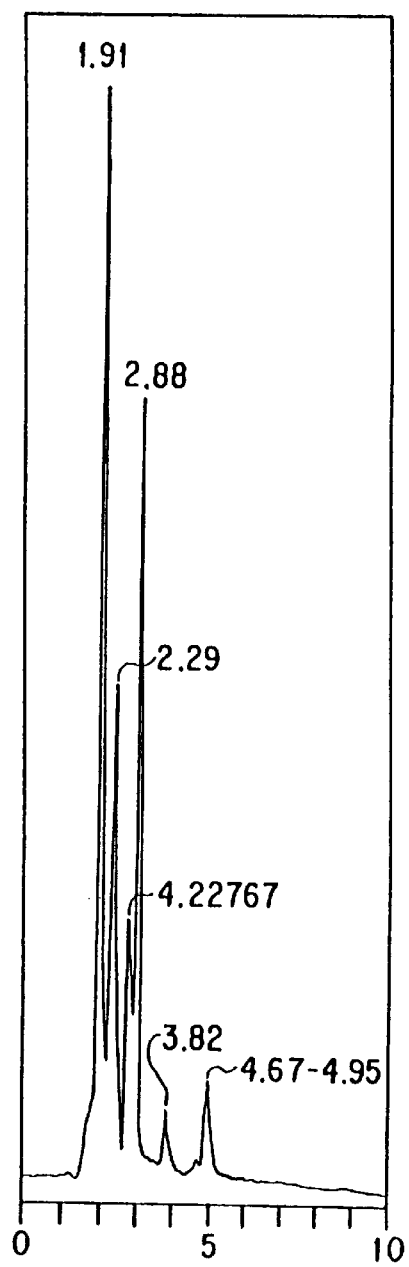
Figure 2:
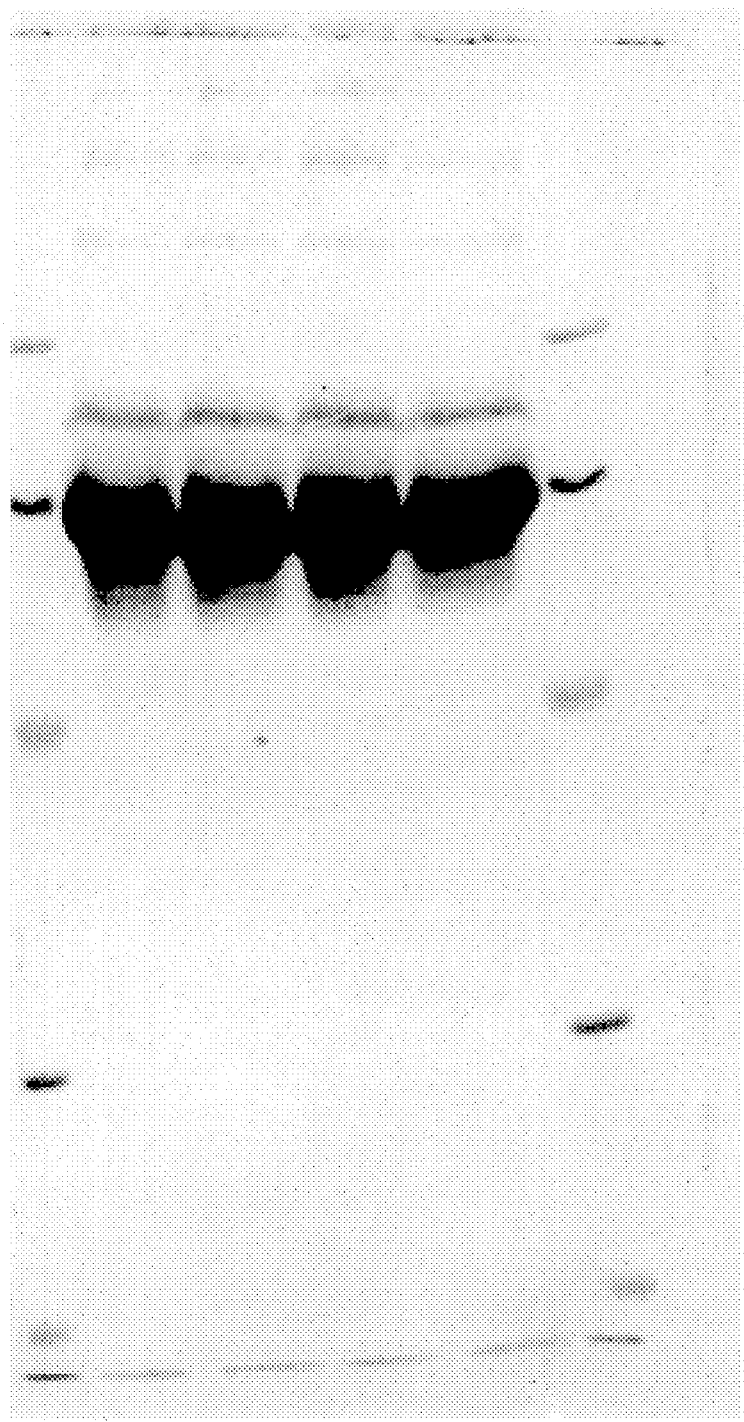
Figure 3:
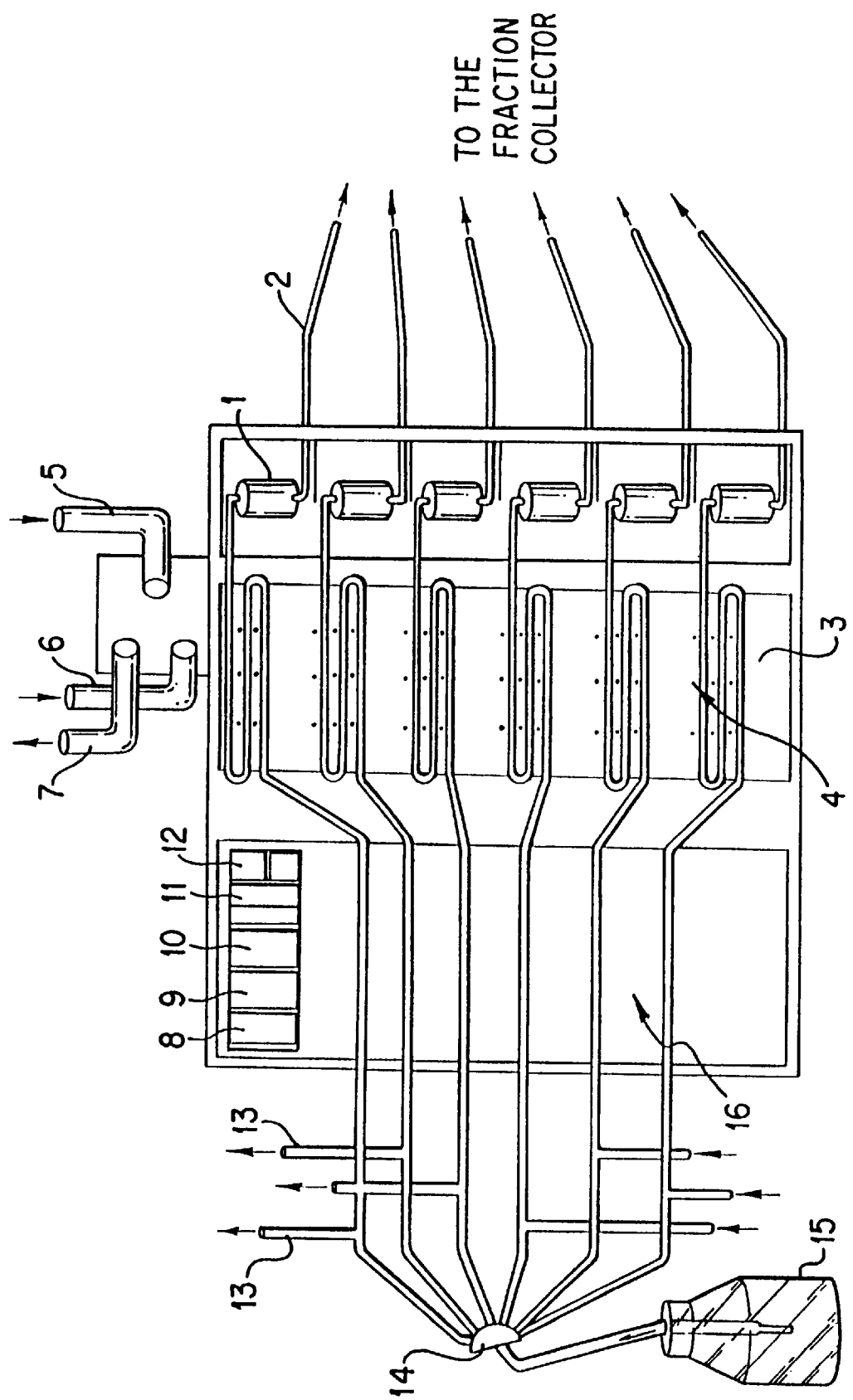
Figure 4A:
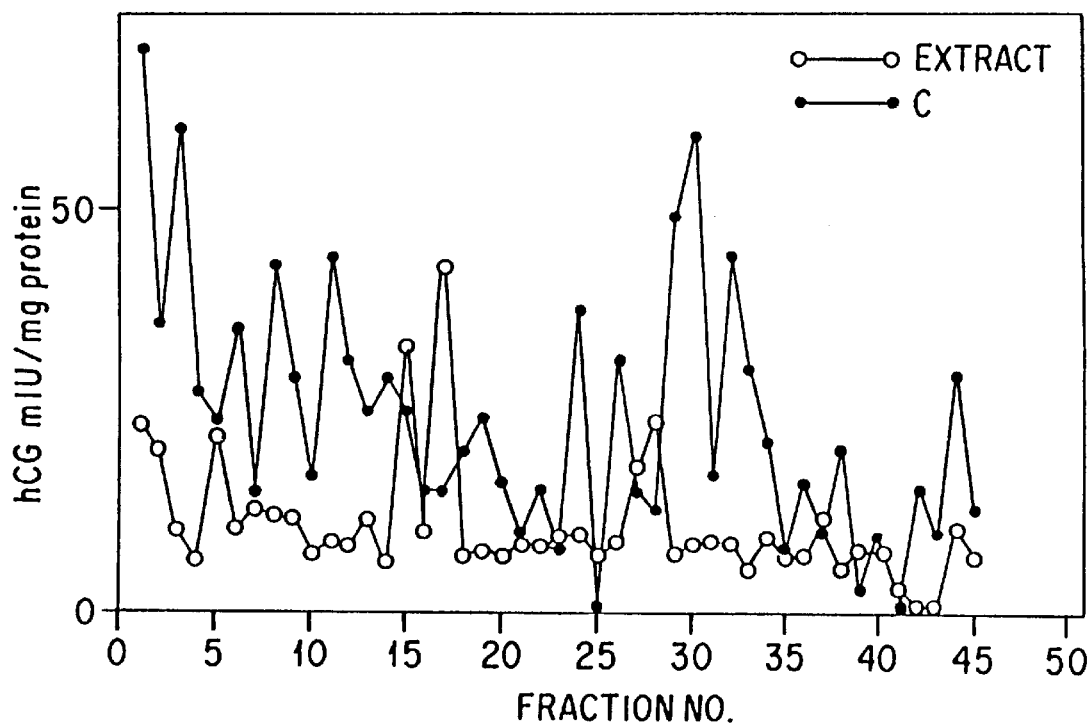
FIG. 4A shows the ability of extract to suppress hCG secretion. As FIGS. 4B and 4C illustrate, the ability of short pulses of the <8,000 MW fraction to inhibit hCG secretion (FIG. 4B) is eliminated by heat inactivation at 57° C.

HPLC analysis was performed as set forth in Section 6.1.3., supra. See FIG. 11.

8.2. RESULTS AND DISCUSSION 8.2.1. GPA-1 CAUSES INCREASED SECRETION OF HCG BY PLACENTAL EXPLANTS

Figure 10:
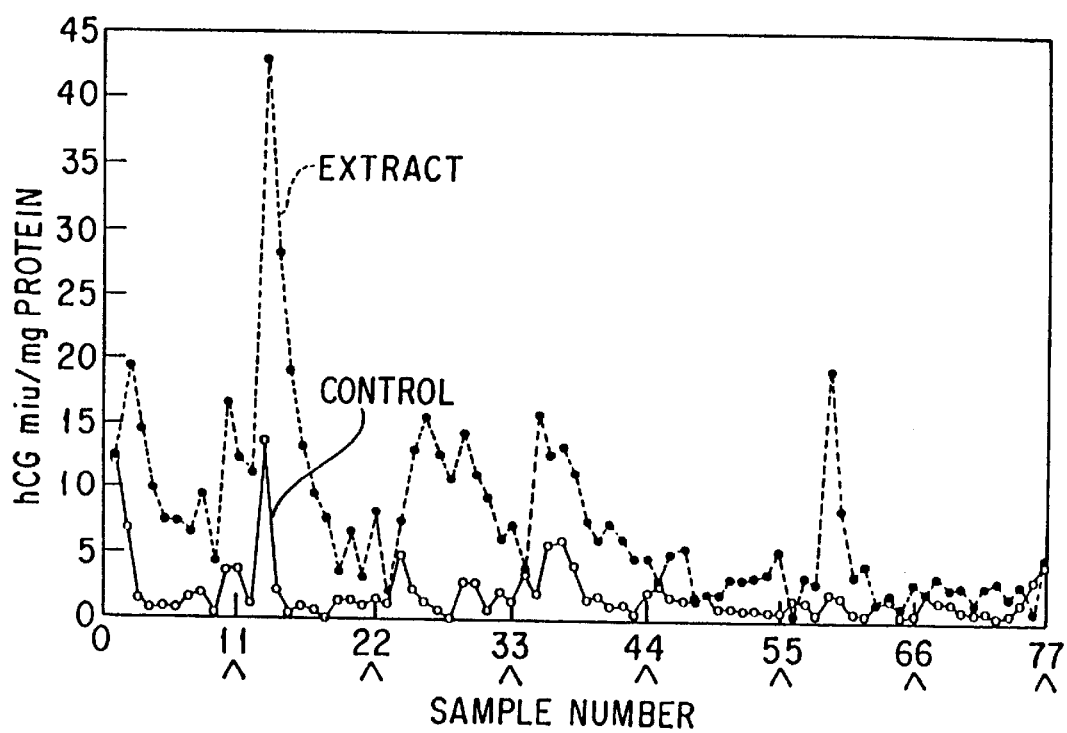

It was observed that the <3,000 MW fraction, containing a protein termed GPA-1, of extract was able to increase hCG secretion by placental explants. Normally, hCG is secreted by placental extracts in a spontaneous pulsatile fashion with a relatively stable frequency. When a one minute pulse of the <3,000 MW fraction was administered to explants via the super-fusion apparatus, a major increase in hCG secretion was observed, as shown in FIG. 10. This was evidenced by a four-fold increase in the area under the curve noted in the channel of the super-fusion apparatus treated with the <3,000 MW fraction compared to the control channel. In contrast, no effect on hCG secretion was observed in the channels treated with the <100,000 MW, <50,000 MW, and <30,000 MW fractions. Of note, treatment of explants with <3,000 MW fraction (GPA-1) which had been heat inactivated at 57° C. for 30 minutes had no effect on hCG secretion. In addition, extraction of the fraction by charcoal/dextran (as is used to extract steroids) also eliminated its activity. 8.2.2. GPA-1 PROMOTED MORULAR DEVELOPMENT The number of morula treated with the <3,000 MW fraction (GPA) that matured to form blastocysts was about three-fold greater than the number of blastocysts formed by morulas treated with buffer only. This observation occurred when morulas were treated with 10 microliters of GPA-1, which has a protein content of about 0.2 µg/ml. Exposure of the embryos to 50 microliters of GPA-1 containing fraction was found to increase the survival of the blastocysts by a factor of two relative to control, as measured over a 48 hour period.

Heat inactivated GPA-1 failed to affect morular development.

8.2.3. GPA-1 PROMOTED TROPHOBLAST DEVELOPMENT

When trophoblast development was evaluated using collagen-coated culture dishes, it was observed that the same level of development achieved by normal controls within 24 hours had been achieved by GPA-1-containing fraction-treated embryos within only 14 hours. These developmental changes included adhesion of the blastocyst to the collagen surface and penetration of the collagen by the differentiating trophoblastic cells. The process accelerated in vitro by GPA corresponds to the in vivo implantation process, and indicates that GPA-1 may be used to facilitate implantation, and, hence, increase fertility, in human beings.

9. EXAMPLE: JDK-AP1 AND JDK-AP2 PROTEINS 9.1. MATERIALS AND METHODS 9.1.1. MATERIALS

Methyl-[$^3$H]-thymidine (93 Ci/mmole) was obtained from Radiochemical Centre (Amersham, England). Dulbecco's modified Eagle's medium (DMEM), trypsin-EDTA solution (0.25% to 0.02%), phenyl-methyl-sulfonyl-fluoride (PMSF), diethyl-triethol (DTT) and Tris buffer solution were obtained from Sigma (St. Louis, Mo., USA). Fetal calf serum (FCS) was obtained from Biochemical Industries (Beth-Haemek, Israel).

9.1.2. TISSUE PREPARATION

After obtaining appropriate consent, elective pregnancy terminations were carried out in the first trimester. Collected tissue was placed on ice for further processing. Spinal cord and brain tissue were removed using microsurgical technique (Barnea, et al., 1989, *Placenta* 10, 331–344) Porcine embryos (5 to 10 cm, corresponding to 40 to 70 days of gestation) obtained from a slaughter house were immediately placed on ice and subsequently transferred to the laboratory for processing. The brain and spinal cord tissues were dissected out on ice using microsurgical techniques as previously noted. Tissue was extracted and sonicated in 0.2 M Tris buffer 1 mM of PMSF and 2 mM of DTT (pH 7.4), centrifuged at 20,000 rpm. The supernatant was filtered through 0.2 µm filters.

9.1.3. CHROMATOGRAPHIC METHODS

Phase I EPLC Gel Filtration (based on molecular size). The samples were applied to an HPLC column (Superdex 75 HR 10/30, LKB, Pharmacia, Piscataway, N.J.) which was previously equilibrated with the same buffer. Samples of 0.5 ml were collected at a flow rate of 0.5 ml/min and frozen at −70° C. until used. The procedure was subsequently scaled up using a TSK HW55 16/570 mm column, and 3 ml batch samples were applied. The MW of the various fractions were estimated from the retention time of proteins with known MW. Their protein content was estimated by their absorbance at 280 nm. The active fractions were concentrated using a Microsep (Filtron, Northborough, Mass.) with a <3 kDa cut-off filter.

Phase II HPLC (based on protein charge). The concentrated sample was applied to an ion exchange column TSK-DEAE [Merck Fractogel 650 (M) 160/90 mm] which was equilibrated with 0.1 M Tris buffer containing 308 mg DTT/L at pH 7. The gradient flow was 1.5 ml/min, and 1.5 ml fractions were collected and tested.

Phase III HPLC Reverse Phase (based on protein hydrophobicity). A C18 preparative column (Vydac) was used for further purification. Samples were run in a 0.1% TFA acetonitrile buffer, and samples were collected every minute. Recovered samples were twice evaporated and resuspended in water.

Phase IV HPLC Reverse Phase PhenyL. The active fraction was further applied to a phenyl reverse phase C-4 column, and samples of 1 ml/min were collected and tested.

9.1.4. CELL LINES AND CULTURE CONDITIONS

The cell lines used were: (1) human breast cancer cell line MCF-7 (Pagliacci, M. C., et al., 1991, *Endocrinol.* 129, 2555–2562; Berthois, Y., et al., 1989, *Biochem. Biophys. Res. Commun.* 159, 126–131); (2) rat osteosarcoma cell line ROS clone 17/2.8 (Majeska, R. J., et al., 1980, *Endocrinol.* 107, 1494–1503; Pines, M., et al., 1986, *Biochem. Pharmacol.* 35, 3639–3641); (3) Rat-1, an established SV40-transformed rat embryo fibrosarcoma cell line (Pines, M., et al., 1986, *Bone and Mineral* 1, 15–26); (4) MCO$_5$, rat fibrosarcoma cell line; SGL/J mice radiation-induced acute myeloid leukemia (RI-AML) cell line (Resnitzky, P., et al., 1985, *Leukemia Res*, 9, 1519–1528); (5) B16F1O mouse melanoma cell line; and (6) Balb/c 3T3 cell line (Steinberg, B., et al., 1978, *Cell* 13, 19–32). Cells were cultured in DMEM containing 5% FCS at 37° C. with 95% air and 5% CO$_2$. RI-AML cells were cultured in DMEM with 10% FCS and 10$^{-5}$M mercaptoethanol. Cells were detached by addition of trypsin-EDTA medium, centrifuged, resuspended in DMEM with 5% FCS, plated in 1 ml wells, and allowed to resume development for 1 to 3 d. Subsequently, various concentrations of test compounds were added for 1 to 4 d. In addition, normal primary human skin fibroblasts were cultured in DMEM containing 10% FCS, detached from the dishes by addition of trypsin-EDTA solution, and plated in wells. After 24 h, various concentrations of the test compounds were added for 4 d. Cultures containing buffer alone served as controls in all experiments.

9.1.5. CELL PROLIFERATION ASSAYS

Direct measurement of cell number was made after incubation for 2 to 4 d with the various test compounds by detaching the cells using trypsin-EDTA and counting using a cell counter (Coulter Electronics, Luton, England) or manual counting. Cell viability following culture was determined using trypan blue staining.

9.1.6. [³H]-THYMIDINE INCORPORATION

In other experiments, following incubation for 2 to 4 d, fresh media containing 1 μCi/ml [³H]-thymidine was added for 4 h. The media was then discarded, detached cells were centrifuged, 4% perchloric acid was added, and the DNA-bound [³H]thymidine was counted using a scintillation counter (Pines, M., et al., 1988, *J. Cellular Biochem.* 37, 119–129).

9.1.7. MTT ASSAY

Proliferation of MCF-7 cells was also measured using the microculture 3-(4,5-dimethylthiazol-2-yl)-2,5-diphenyltetrazolium bromide (MTT) assay (Alley et al., 1988, *Cancer Res.* 45, 589–601). Cells ($3 \times 10^3$) were cultured in 96-well plates, and test compounds or buffer were added. Growth inhibition was quantified after 4 d following the reduction of tetrazolium dye to a formazan by the surviving cells and measuring absorbance at 570 nm using a Vmax plate reader (Molecular Devices, Menlo Park, Calif.). Results were calculated by plotting against a standard curve generated by plating increasing numbers of cells.

9.1.8. GEL ELECTROPHORESIS

Human and porcine embryonal neural tissue fractions were run on SDS-PAGE (20%) in NaDoSO, (Gierschik, et al., 1985, *Proc. Natl. Acad. Sci. USA* 82, 4095–4099). Gels were run in a constant current (30 mA) for 4 h with pre-stained MW markers and stained for proteins by Coomassie Blue or silver stain. Samples were run on a gel following each HPLC column separation. 9.1.9 STATISTICAL ANALYSIS The data was evaluated by Duncan's multiple range test for comparison of multiple groups; p<0.05 was considered to be statistically significant. Data are representative of experiments which were carried out in quadruplicate. Results represent the mean ± SE of four wells of two or more separate experiments yielding similar results.

9.2. RESULTS

9.2.1. INHIBITORY EFFECT OF HUMAN JDK-AP

Figure 12:
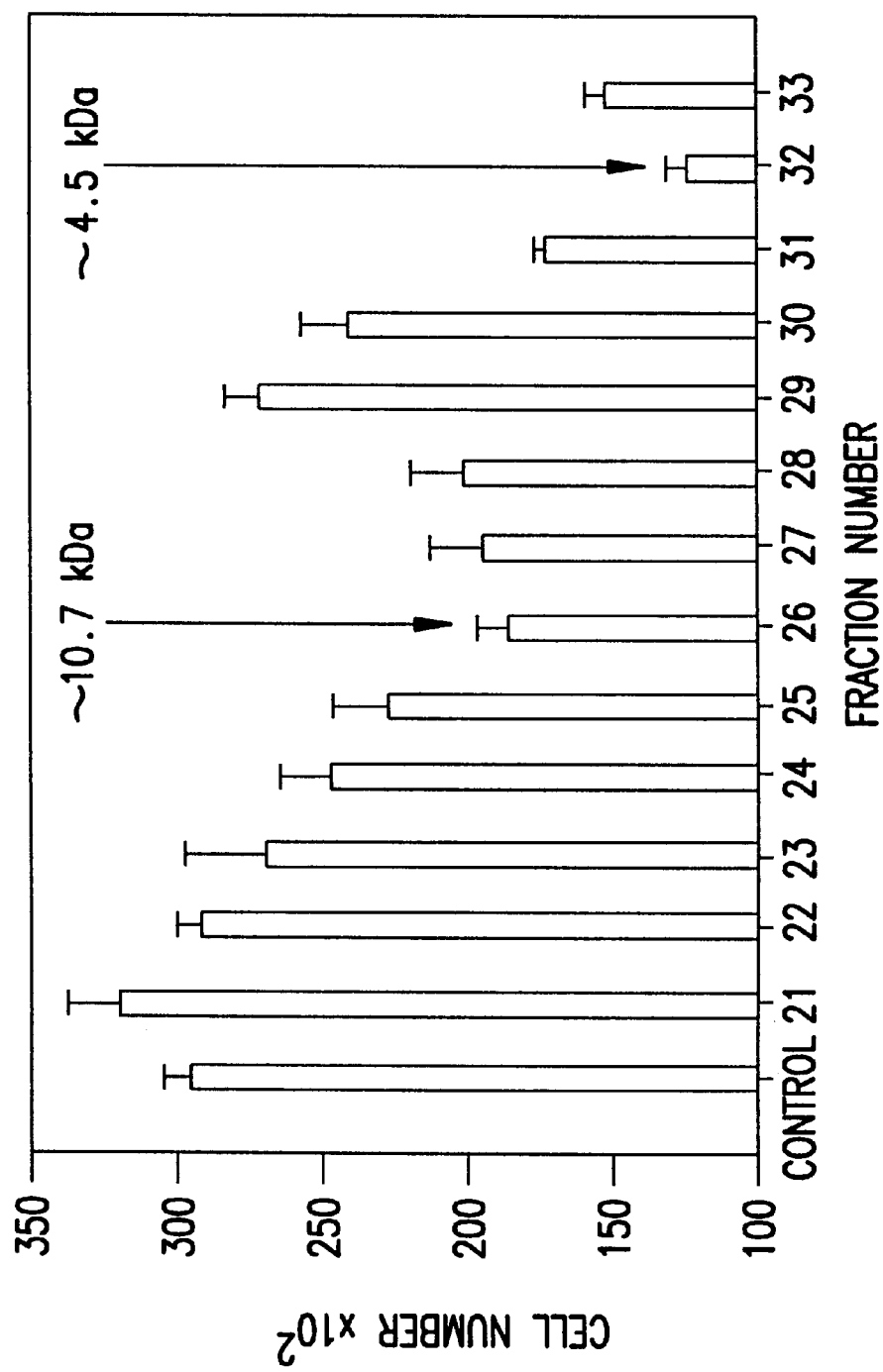

Various fractions from the 2 to 35 kDa region of human embryonal brain were separated by Phase I HPLC and added to MCF-7 cancer cells for 4 d. Results showed statistically significant and highly reproducible reduction in cell numbers of 65% and 40%, respectively, with JDK-AP1 (fraction 32, ~4.5 kDa) and JDK-AP2 (fraction 26, ~10.7 kDa) (FIG. 12). Neither the addition of total extract nor buffer alone affected cell count. In contrast, certain fractions (<3 kDa) significantly enhanced cell proliferation.

Figure 13A:
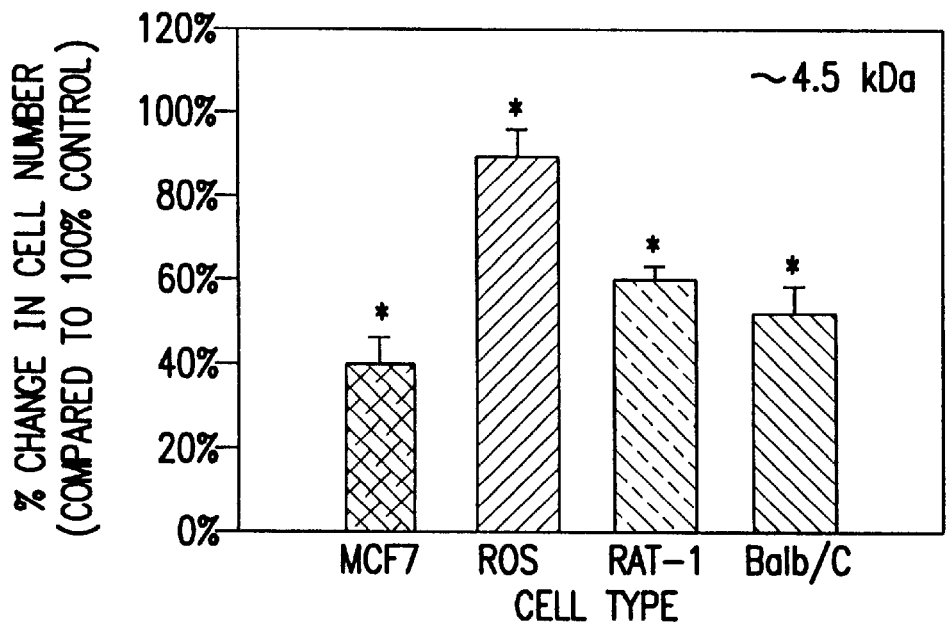
Figure 13B:
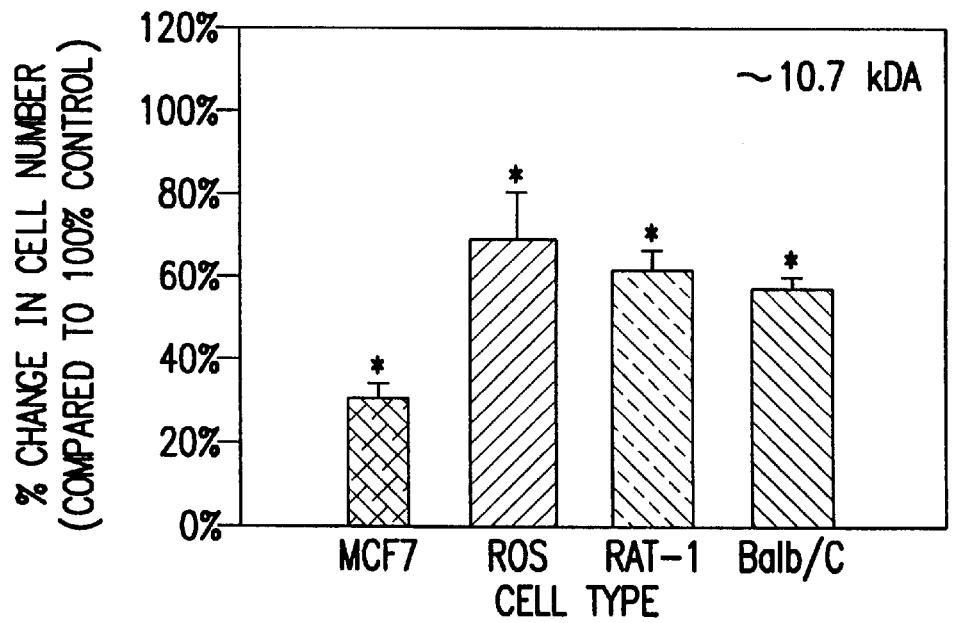
Figure 13C:
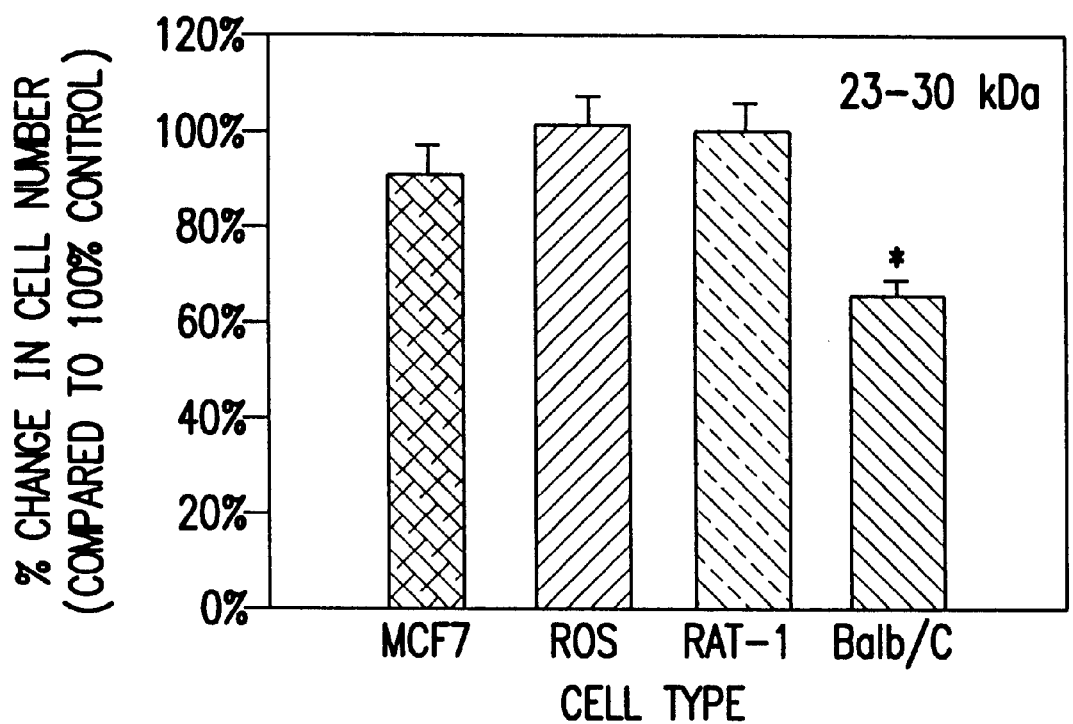

FIGS. 13 A and B show that addition of JDK-AP1 and JDK-AP2 significantly reduced proliferation of various malignant and transformed cell lines following incubation for 4 d when compared to the total tissue extract and buffer alone. FIG. 13 C shows that, with the exception of Balb/c 3T3, the 23 to 30 kDa fractions had no effect on cell proliferation. The addition of JDK-AP1 and JDK-AP2 for 2 d also caused a significant decrease in [³H]-thymidine incorporation by MCF-7 cells (Table IV). MCF-7 cells were plated in dishes containing DMEM and 5% FCS, and were allowed to develop for 2 d. Media was subsequently discarded, fresh media was added, and cells were incubated with JDK-AP fractions (1 μg protein/ml or buffer) for 2 d. [³H]-thymidine (1 μCi/ml) was subsequently added for 4 h. Media was subsequently discarded, cells were washed and detached, and the 4% perchloric acid precipitate was counted.

TABLE IV

Inhibitory effect of human embryonal spinal cord fractions on [³H]-thymidine incorporation by MCF-7 cells. Data represents the mean ± SE percent change compared to control.

| Treatment | % [³H]-thymidine |
|---|---|
| Control | 100 ± 5 |
| JDK-AP2 | 89 ± 3* |
| JDK-AP1 | 87 ± 4* |

*p = <0.05

9.2.2. INHIBITORY EFFECT OF PORCINE JDK-AP

Figure 14:
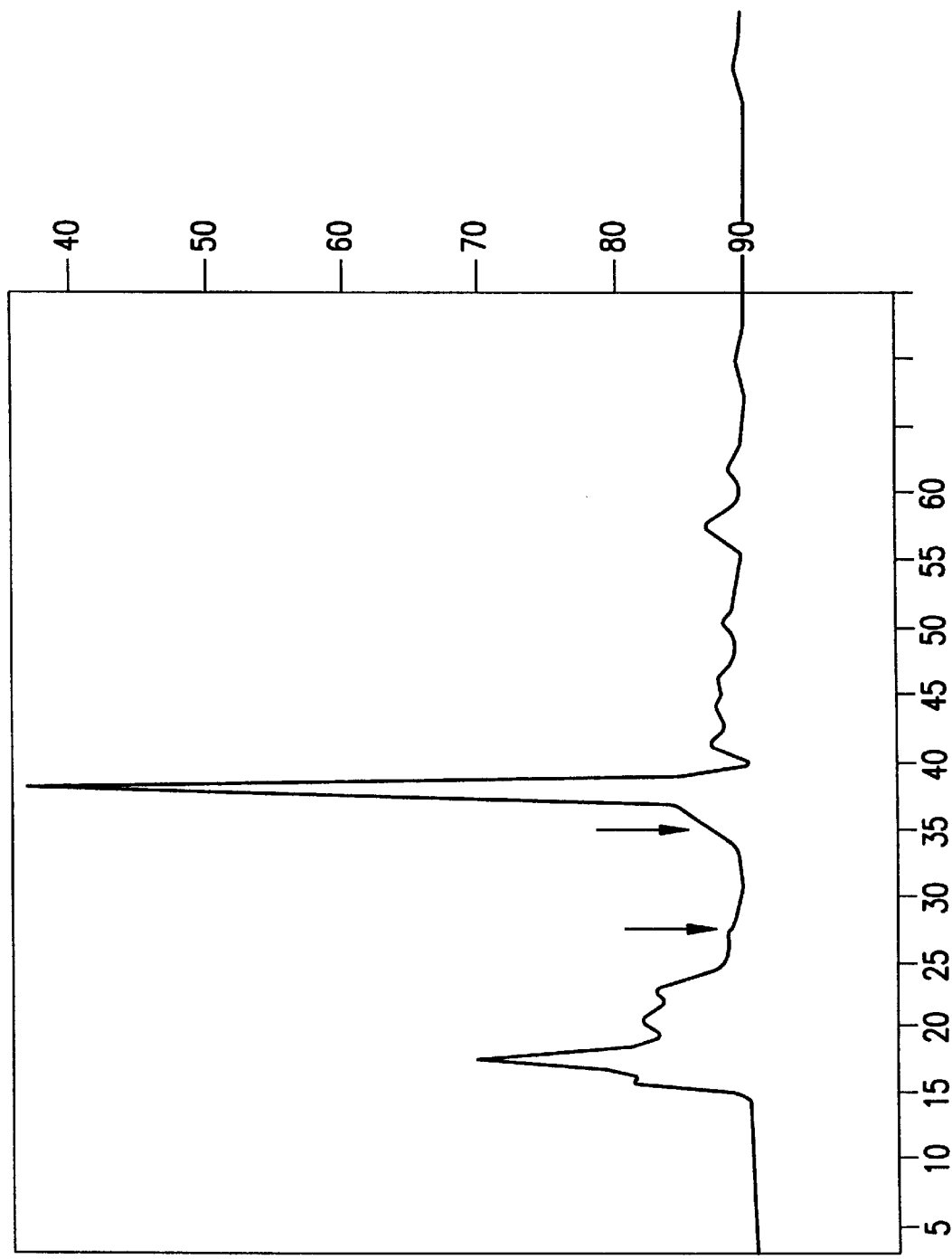
Figure 15:
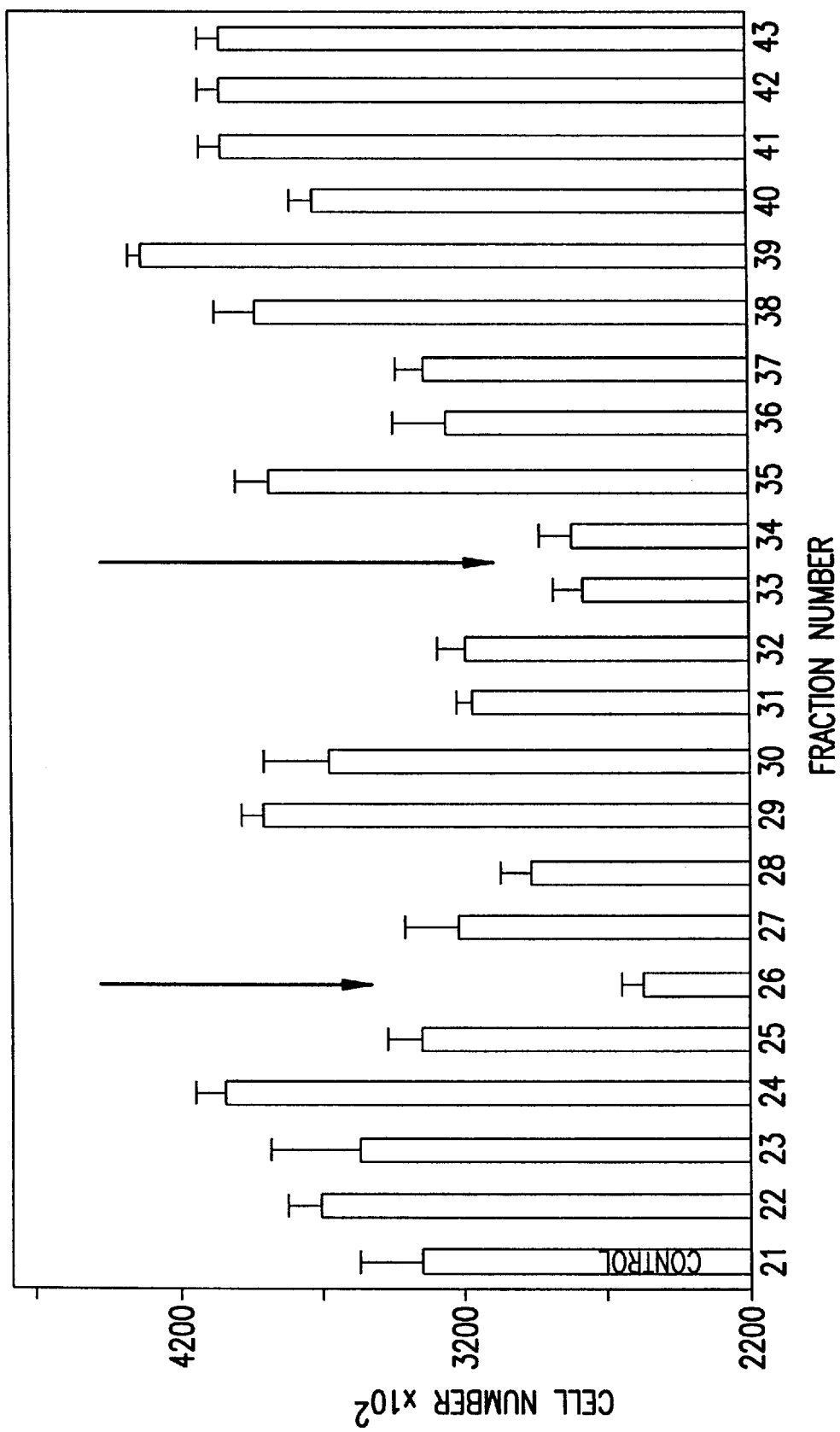

Inhibitory Effect on Cell Count. Using methodology similar to that employed with human-origin tissue, porcine embryonal neural tissue was separated by gel filtration HPLC (FIG. 14), yielding similar activity and results for both porcine JDK-AP1 and JDK-AP2 as measured by the proliferation of MCF-7 cells (FIG. 15).

Inhibitory Effect on Thymidine Incorporation. Porcine JDK-AP1 and JDK-AP2 also inhibited [³H]-thymidine incorporation by MCF-7 cells (~20%) within 4 d. [See also FIG. 28.]

Inhibitory Effect using the MTT Assay. Incubation with both porcine JDK-AP1 and JDK-AP2 caused a significant decrease (53% and 71%, respectively) in MCF-7 cell proliferation after 4 d as measured by the MT-F assay.

Gestational Age-dependent Effect. FIGS. 15 A and B show the statistically significant (40%) inhibitory effect of the spinal cord and brain JDK-API and JDK-AP2 of porcine embryonal neural tissue on MCF-7 cell proliferation following incubation for 4 d compared to buffer alone used as control. Gestational age-dependent differences were noted with the JDK-AP1 spinal cord fraction: while there was no effect using the 40-day fraction, a significant inhibitory effect was present with the 70-day fraction. Neither the total extract nor the 23 to 30 kDa fractions had a significant effect on cell proliferation (FIG. 15C).

Figure 16A:
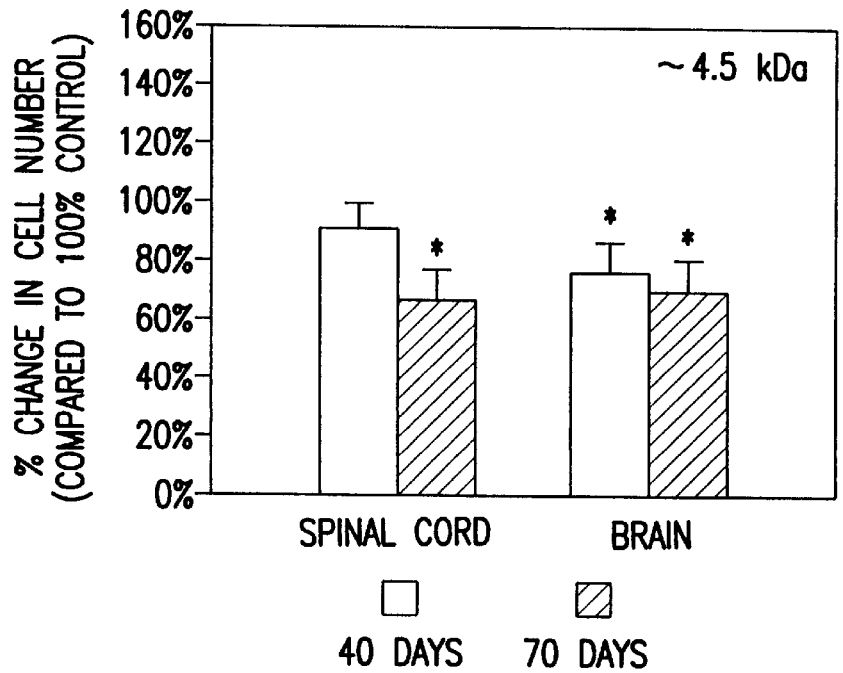
Figure 16B:
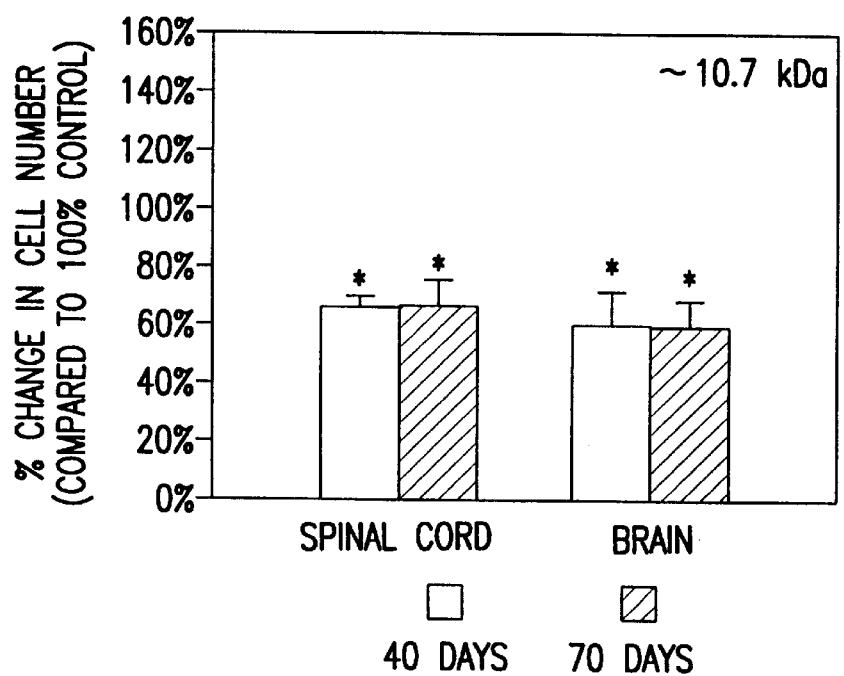
Figure 16C:
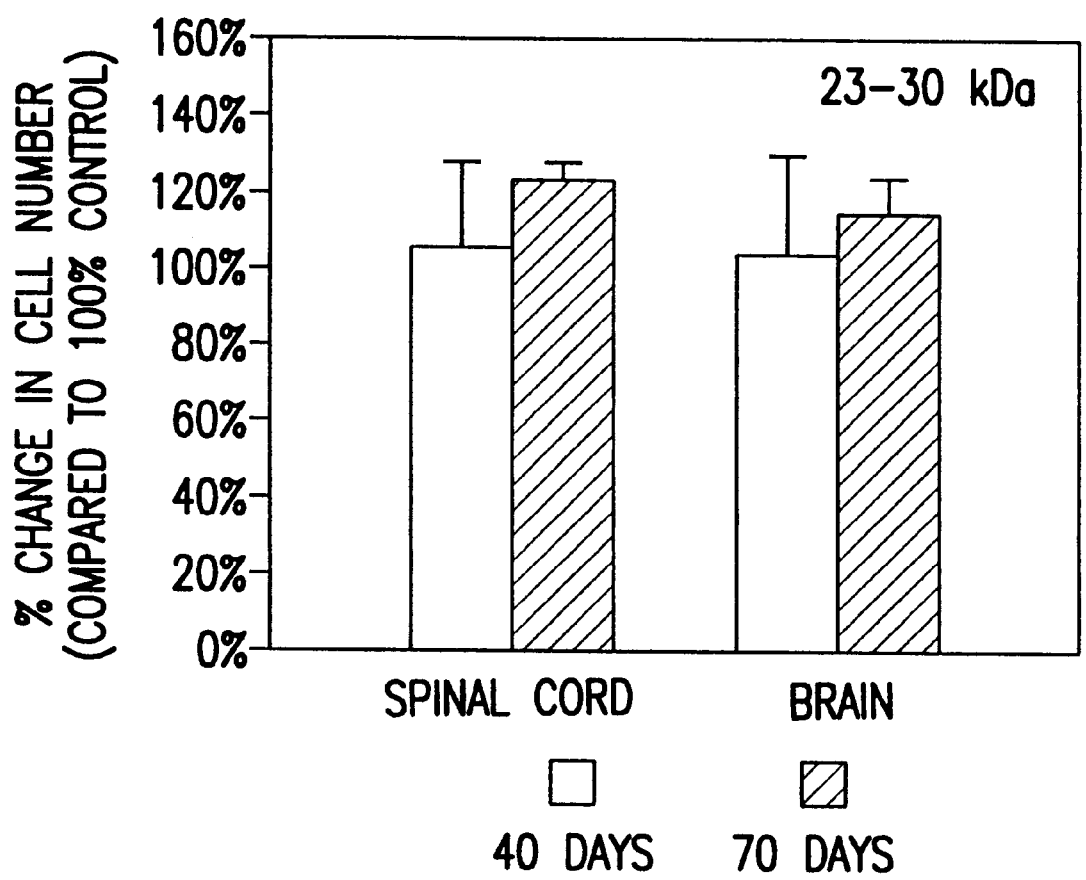

Dose-dependent Effect. FIG. 16 shows the dose-dependent inhibitory effect of filtered JDK-AP2 on MCF-7 cell proliferation after addition to culture for 4 d. The fraction was filtered prior to culture, thus eliminating the buffer while allowing sample concentration. While a significant decrease in cell numbers was noted with as little as 0.5 μg/ml, maximal inhibition (58%) was noted at the 5 μg/ml final protein concentration. The inhibitory effect of JDK-AP1 was also dose dependent (27% and 37% for 10 μl and 20 μl, respectively).

Figure 17:
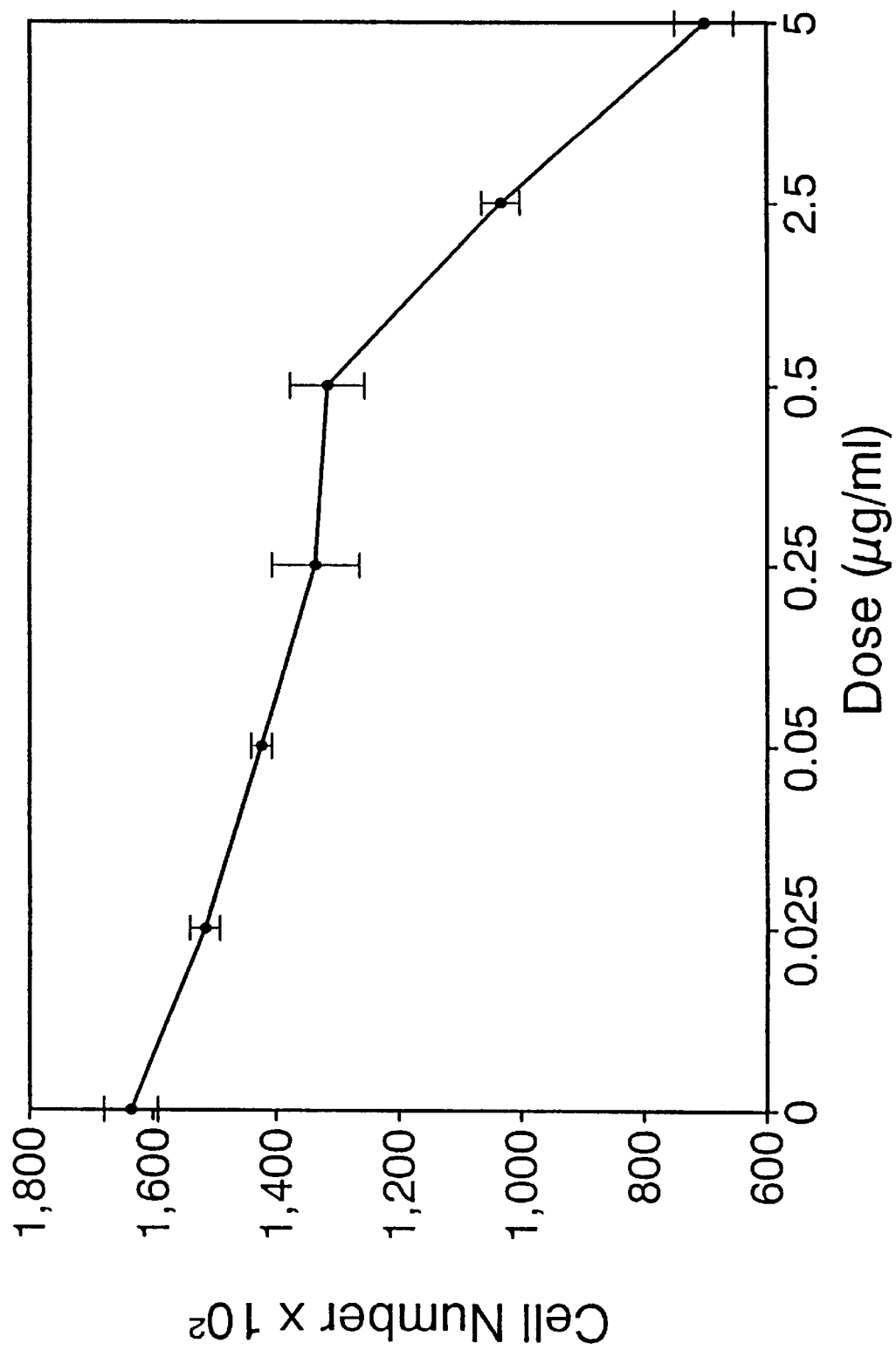
Figure 18:
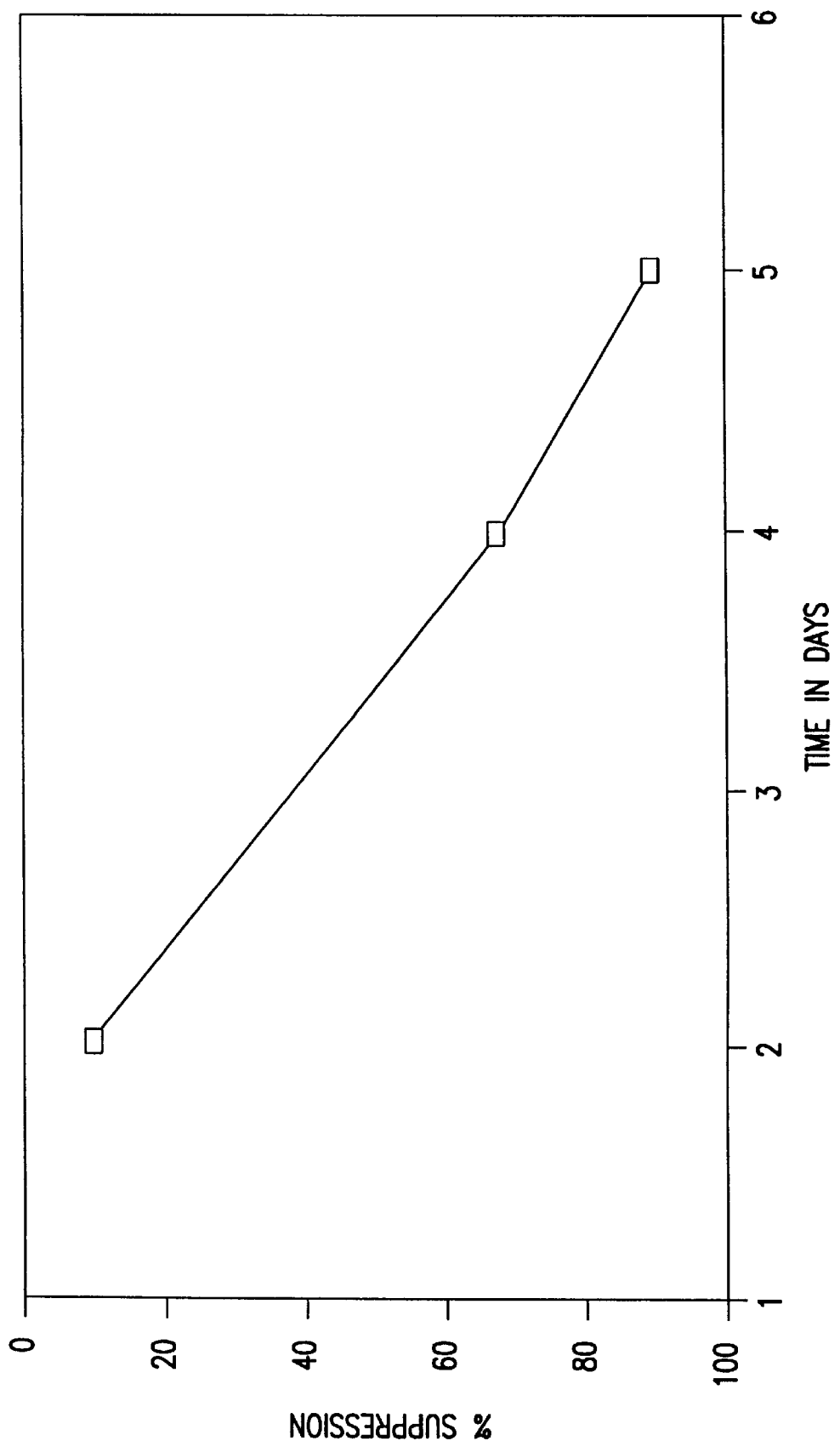

Time-dependent Effect. The time-dependent effect of porcine JDK-AP1 is shown in FIG. 17. While significant inhibition is obtained in as little as 2 d, maximal reduction is generally noted within 5 d of incubation with JDK-AP.

TABLE V

Inhibitory effect of embryonal porcine brain JDK-AP1 (~4.5 kDa) on the proliferation of cultured murine radiation-induced acute myeloid leukemia (RI-AML). Data represents the mean ± SE percent change from control.

| Treatment | % Cell number |
|---|---|
| Control | 100 ± 8 |
| 20 μl JDK-AP1 | 96 ± 2 |
| 40 μl JDK-AP1 | 94 ± 8 |
| 60 μl JDK-AP1 | 66 ± 4* |

* = p<0.05.

Inhibitory Effect on Other Cancer Cell Lines. RI-AML cells were plated in dishes containing DMEM, 10% FCS and $10^5$ M mercap-toethanol, and were allowed to resume development for 2 d. These cells typically tend to loosely attach to the plastic while some remain in suspension. Cells were incubated for 3 d with various concentrations (1 to 3 μg/ml final protein concentrations) of JDK-AP1 (~4.5 kDa) or buffer. Cells were subsequently detached and counted using a Coulter counter. The addition of porcine JDK-AP1 to RI-AML leukemia cells caused a significant reduction (66%) in cell number in as little as 3 d compared to control (Table V). In addition, an inhibitory effect was also observed on the proliferation of B16FlO melanoma, L1210 mouse lymphocyte leukemia, P338D mouse monocyte macrophage leukemia, and LL/2 mouse Lewis lung carcinoma in pilot experiments.

Lack-of Effect on Normal Skin Fibroblasts. The effect of porcine JDK AP1 was also tested on cultured normal primary human skin fibroblasts. Normal primary human skin fibroblasts were plated in dishes containing DMEM and 10% FCS, and allowed to resume development for 2 d. Media was subsequently discarded and fresh media containing DMEM and 5% FCS was added. Various concentrations of JDK-AP1 (1 to 3 μg/ml final protein concentration) were added for 4 d. Following incubation, cells were detached and counted. In some experiments [$^3$H]-thymidine was added 4 h prior to the end of incubation. Subsequently, cells were washed, precipitated with 4% perchloric acid and counted. After incubation for 4 d, no changes in cell number were noted compared to control when measured both by Coulter counter and [$^3$H]-thymidine incorporation (Table VI). The higher concentrations of JDK-AP1 significantly increased [$^3$H]-thymidine incorporation.

TABLE VI

Effect of embryonal porcine brain JDK-AP1 (~4.5 kDa) on proliferation of normal primary human skin fibroblast cells. Data represents the mean ± SE percent change from control.

| Treatment | % Cell number | % [$^3$H]-thymidine |
|---|---|---|
| Control | 100 ± 5 | 100 ± 3 |
| 20 μl JDK-AP1 | 94 ± 12 | 102 ± 7 |
| 40 μl JDK-AP1 | † | 159 ± 10* |
| 60 μl JDK-AP1 | 108 ± 13 | 163 ± 14* |

* = $p<0.05$.
† = not determined.

9.2.3. PURIFICATION OF JDK-AP2

Figure 19:
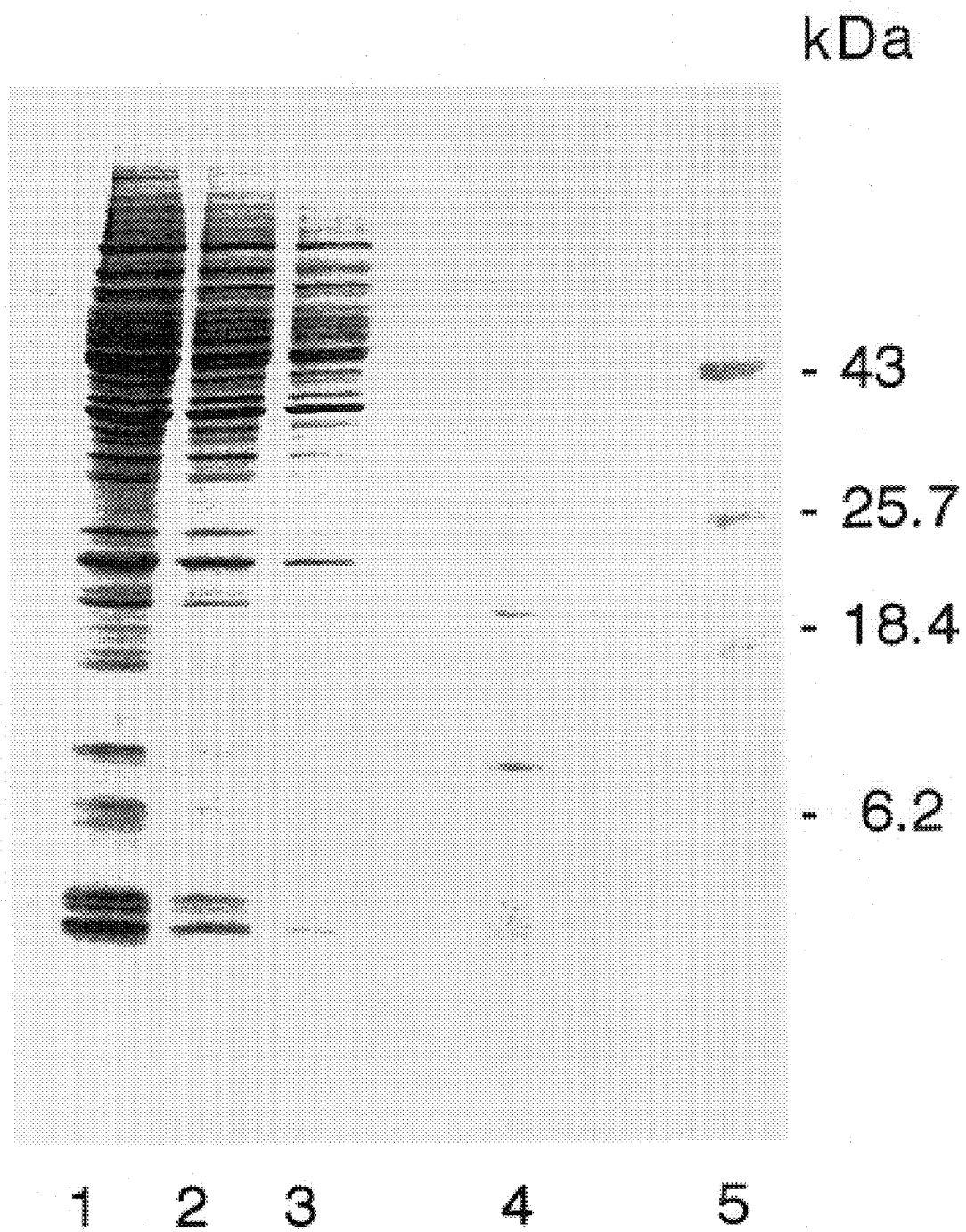
Figure 20:
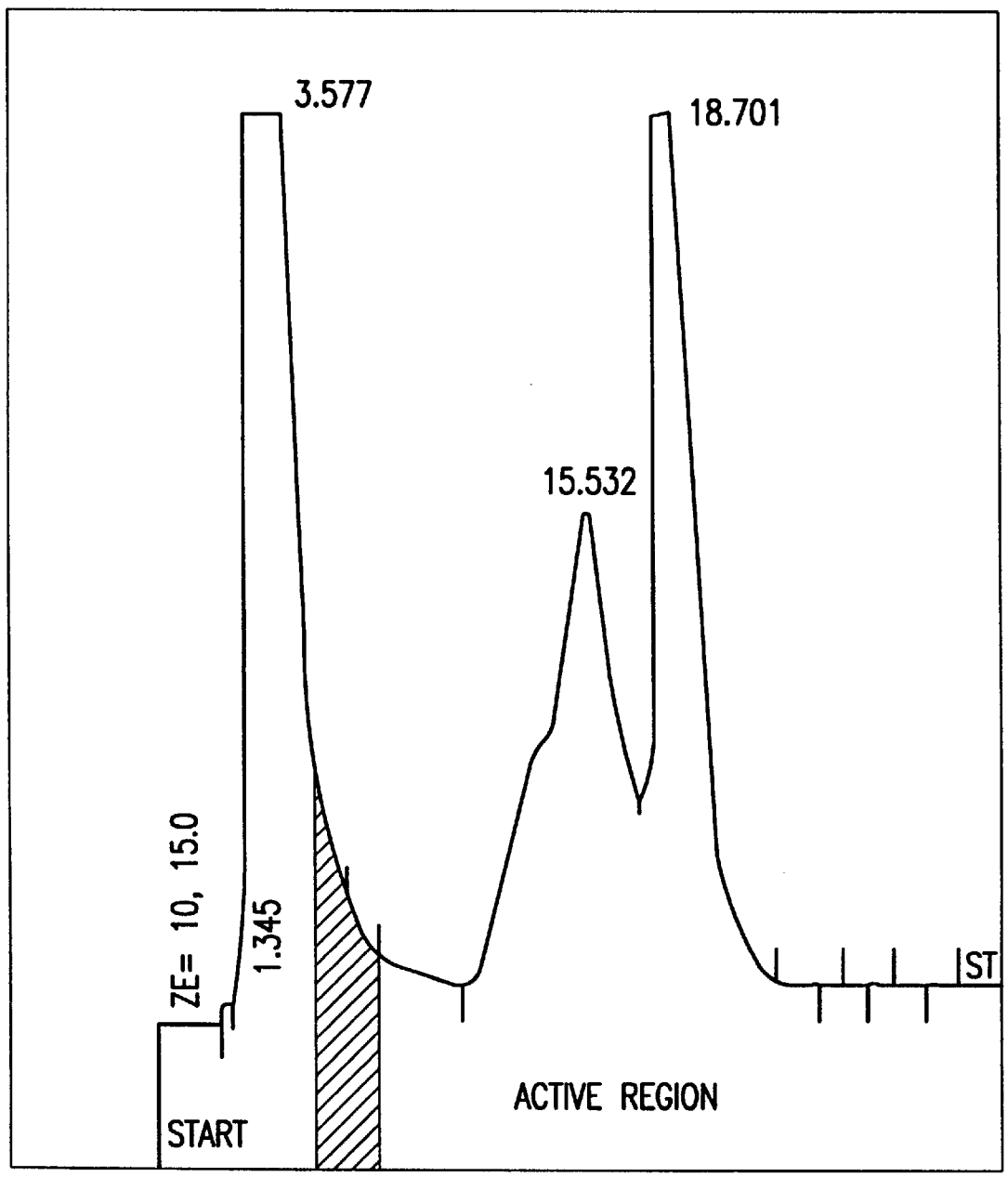
Figure 21A:
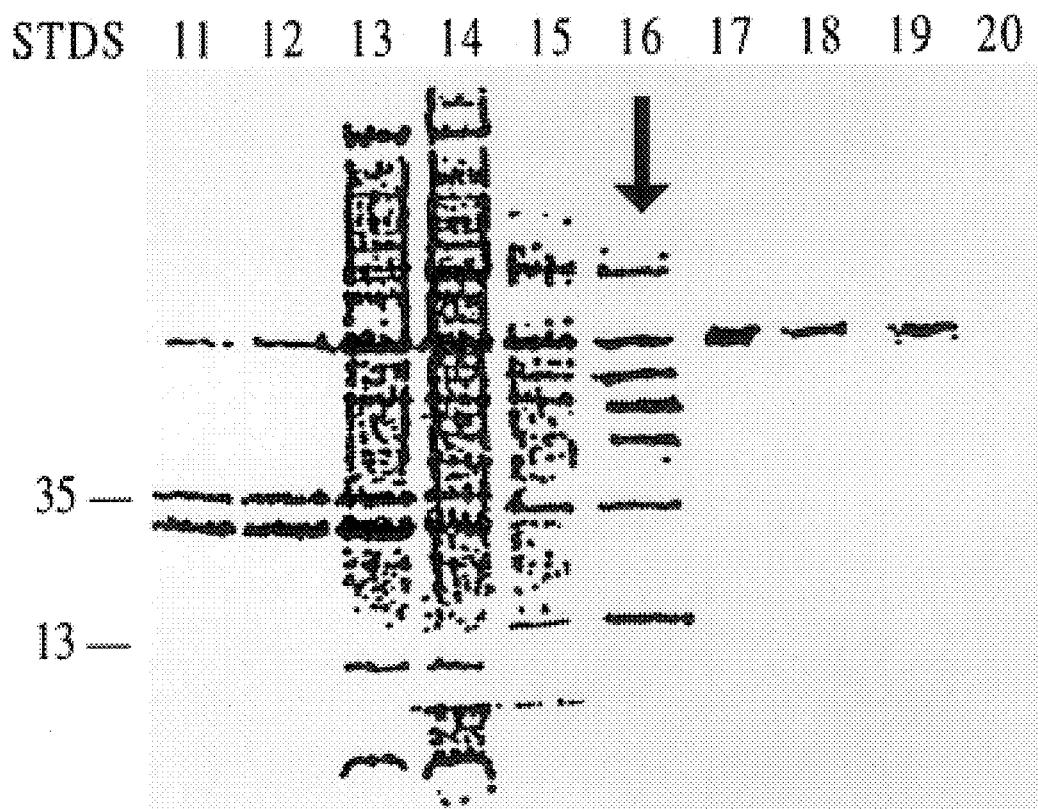
Figure 21B:
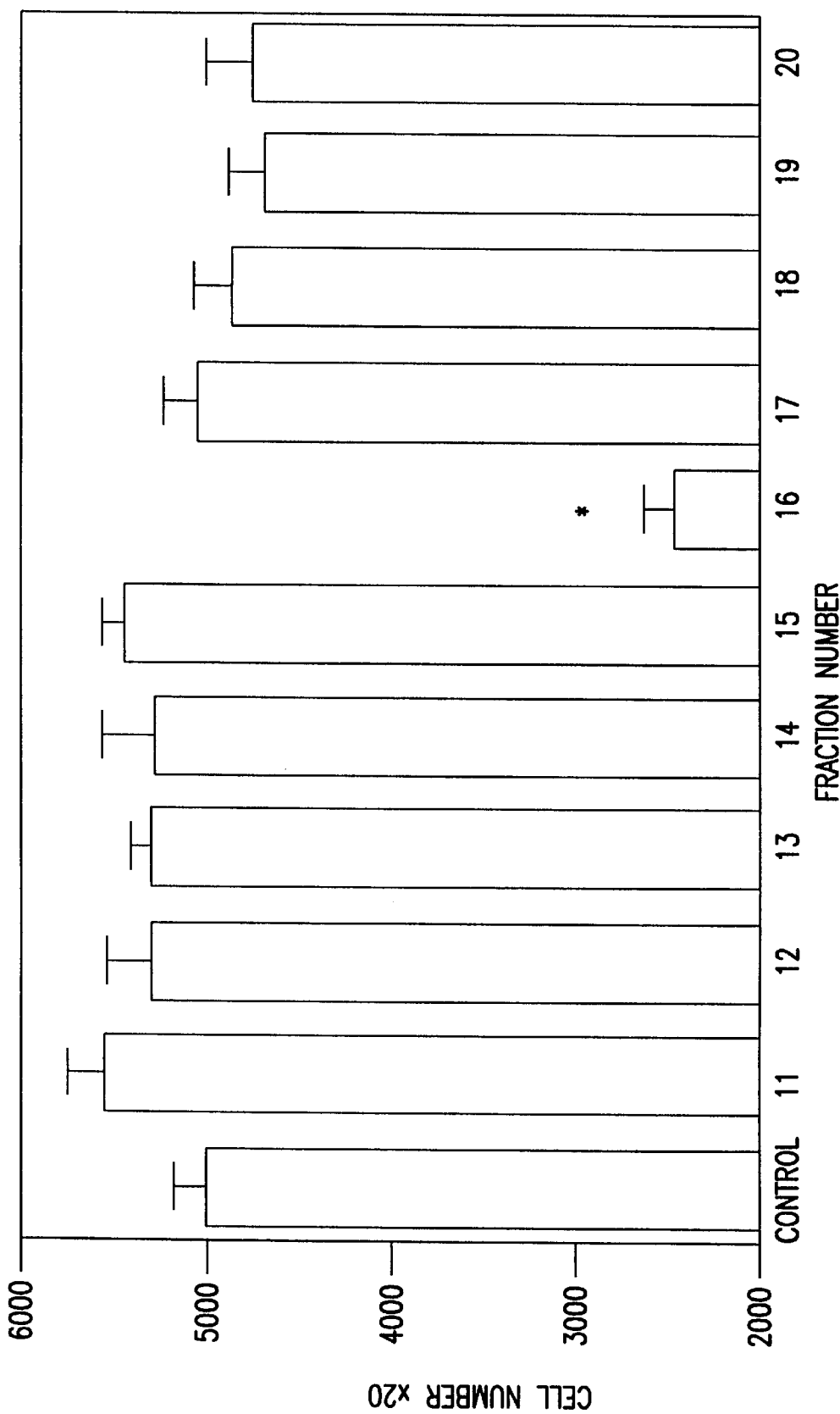

The SDS-PAGE gel electrophoresis profile of the gel filtration HPLC-separated fractions (FIG. 14) revealed 3 to 5 bands in the ~10.7 kDa region (JDK-AP2; FIG. 19). FIG. 20 shows the Phase II HPLC (ion exchange) separation of JDK-AP2. The associated SDS-PAGE gel profile is shown in FIG. 21A. Following separation, significant inhibition of the MCF-7 cells was demonstrated in one fraction compared to controls (FIG. 21B).

Figure 22:
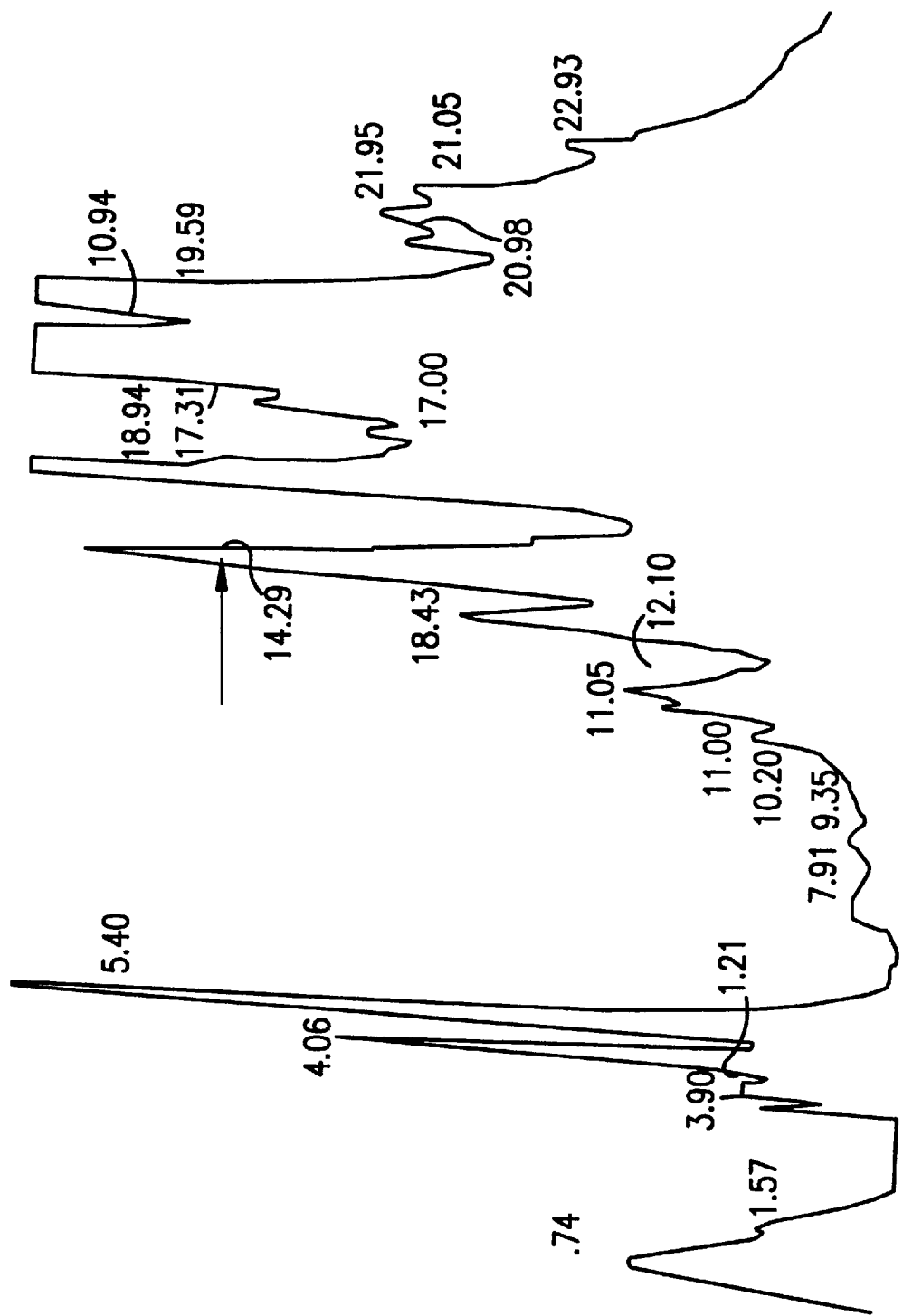
Figure 23:
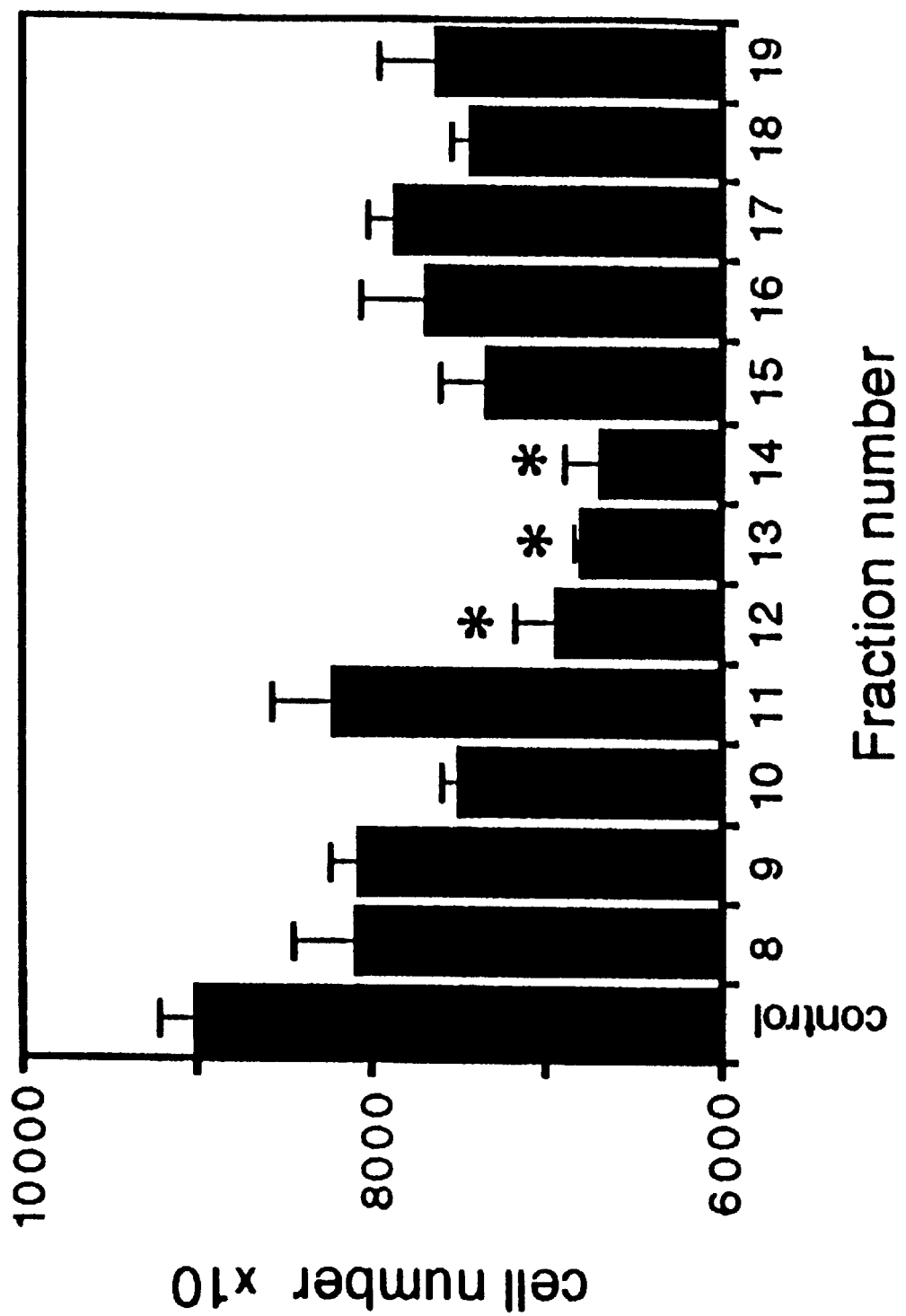
Figure 24:
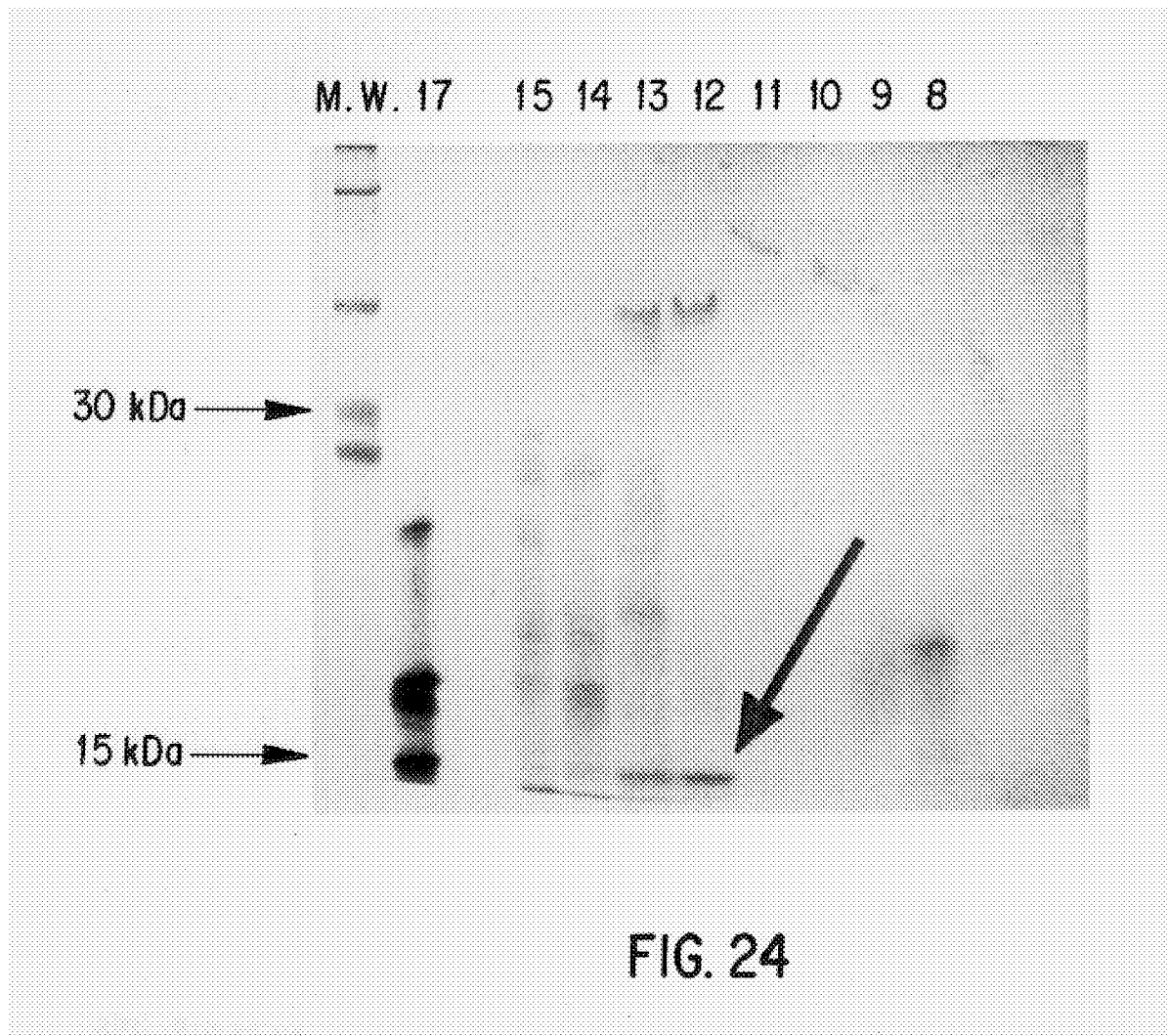

FIG. 22 shows the preparative Phase III HPLC (reverse phase) profile of the active fraction generated by the Phase II column. Significant inhibition of MCF-7 proliferation was observed in the 12, 13, and 14 fractions (FIG. 23). An SDS-PAGE analysis of these peaks revealed 1 to 2 unique bands of 10 to 15 kDa which were absent in the non-active fractions (FIG. 24).

Figure 25:
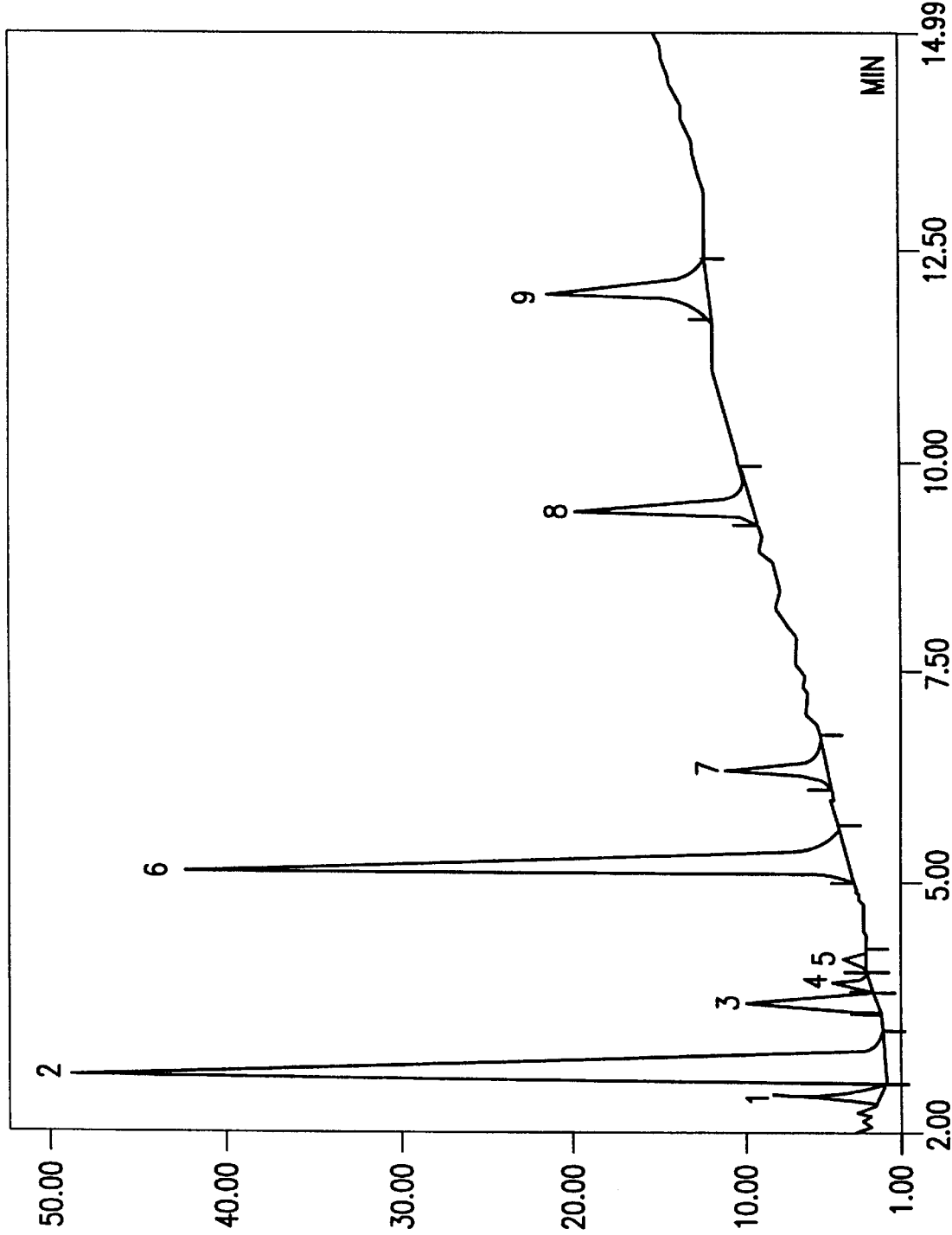
Figure 26:
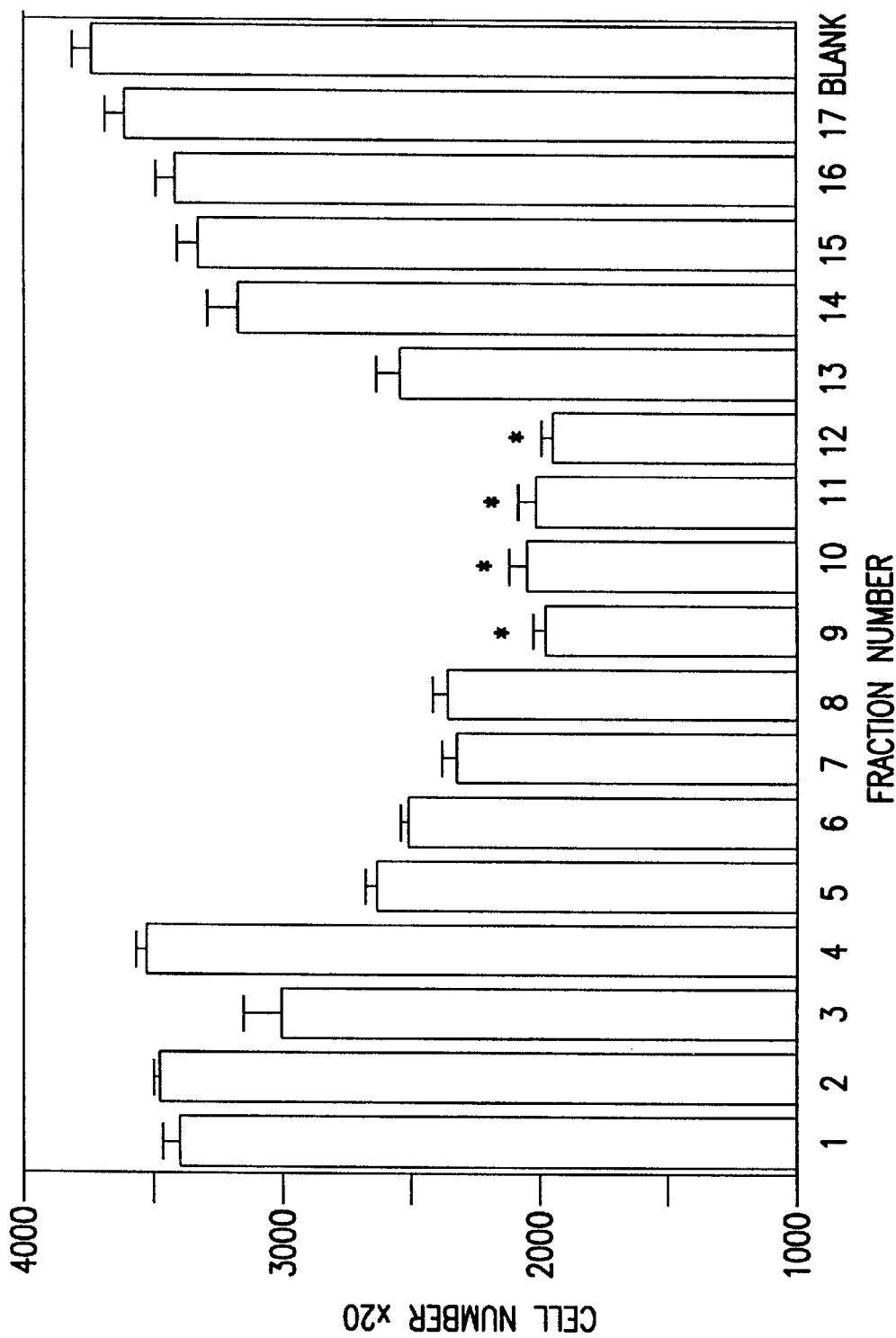

FIG. 25 shows the Phase IV HPLC (phenyl reverse phase) profile of separation of the active Phase III peak. Inhibition of MCF-7 cells can be noted in the region with a low protein content (FIG. 26).

9.2.4. EFFECT OF JDK-AP ON CELL MORPHOLOGY

Micro-photographs (FIG. 27 A through D) illustrate the statistically significant reduction in MCF-7 cell numbers following incubation with the porcine embryonal brain-derived JDK-AP2 (70% reduction) added for 4 d when compared to buffer-treated controls run in parallel. At the end of the culture period cells remained viable (as seen by trypan blue exclusion), tended not to aggregate, and had a fusiform or stellate appearance in many cases. Both JDK-AP1 and JDK-AP2 of human and porcine origin had a similar effect on cell viability and morphology.

9.2.5. CHARACTERISTICS OF JDK-AP

Figure 28:
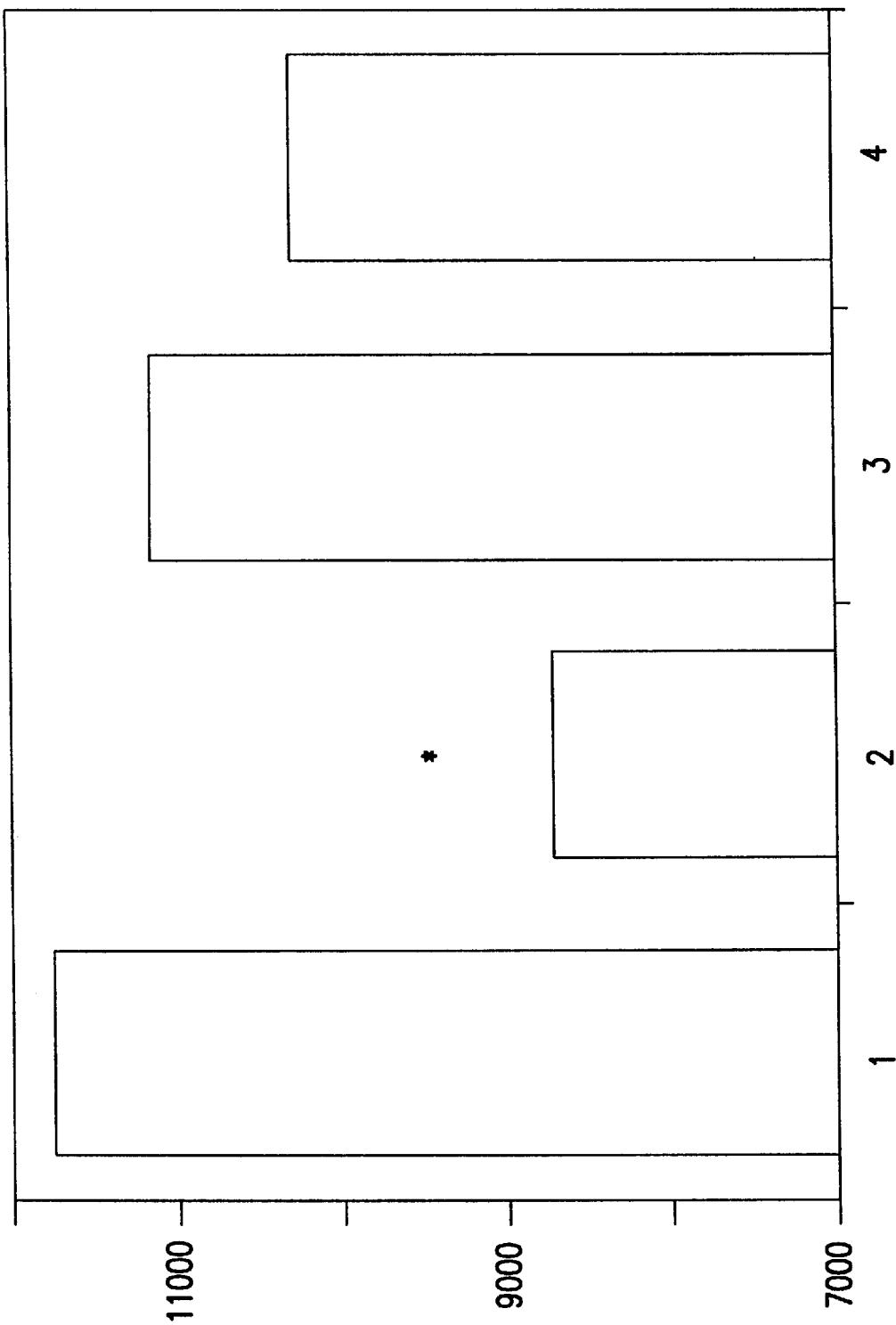
Figure 29:
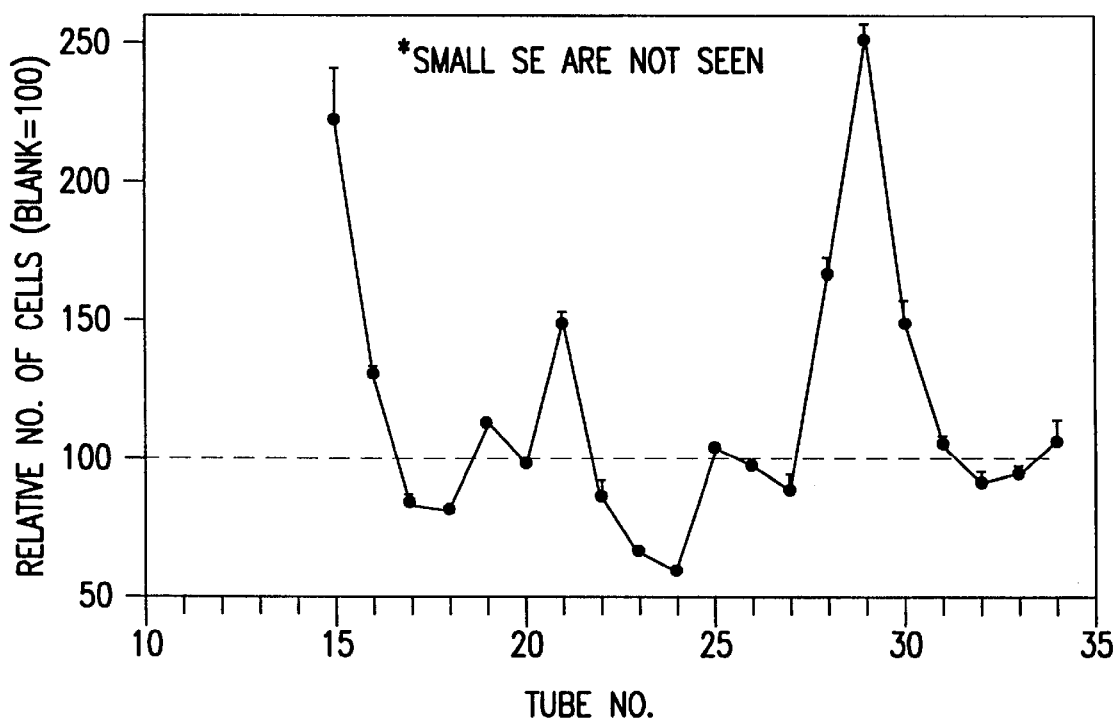

The proteinaceous nature of JDK-AP2 was confirmed by heat inactivation and loss of activity by incubation with proteinase K (FIG. 28). Other characteristics are summarized in Table VII.

TABLE VII

Characteristics of porcine JDK-AP

| | |
|---|---|
| 1. | Soluble in water, Tris-HCl, Hepes, and phosphate buffer; inactive in ammonium acetate |
| 2. | Inactivated by repeated freeze and thaw |
| 3. | Biological activity of both JDK-AP1 and JDK-AP2 is maintained with or without DTT |
| 4. | Induced activity of JDK-AP2 is not due to Interleukin-6 (IL6) since JDK-AP2 is not recognized by a polyclonal antibody against IL6 |
| 5. | High serum level in culture reduces the activity of JDK-AP |

9.3. DISCUSSION

Present data indicates that JDK-AP obtained from mammalian embryonal neural tissue contains factors that represent a novel class of proteins which have significant antiproliferative effects on both human and other mammalian cancer cell lines. Their effect is time- and dose-dependent at very low protein concentrations, and is also dependent on the gestational age of the source material. The significant antiproliferative effect was evidenced by decreased cell count, reduced [$^3$C]-thymidine incorporation and MTT assay. No direct toxic effect was seen; the remaining MCF-7 cell morphology changed and cells remained viable. The effect of JDK-AP was specific since it did not affect proliferation of cultured normal primary human skin fibroblasts. Antiproliferative activity and effect on cell morphology were similar for both the human and porcine JDK-AP fractions. Cross-species efficacy of JDK-AP in reducing cell proliferation was demonstrated: both the human and porcine-origin factors were effective on human breast and rodent cancer cell lines. It is of particular interest to note that JDK-AP was also effective against RI-AML which is considered to be the experimental counterpart of highly resistant human secondary leukemia (Resnitzky, P., et al., 1985, *Leukemia Res*, 9, 1519–1528). Efficacy against sarcomas, including osteo- and fibrosarcoma cell lines, and melanoma was also demonstrated. Further data indicates that JDK-AP2 inhibits the proliferation of lung cancer, cervical cancer and lymphoma cell lines. These results confirm the observations, set forth above, of reduced proliferation obtained by adding semi-purified human JDK-AP to human ovarian and kidney cancer cell lines as well as mouse blastocyst cultures.

Thus far, the efficacy of JDK-AP was demonstrated on a total of 12 different human, mouse, and rat cancer and transformed cell lines. This suggests that the antimitogenic effects of these factors are not organ- or epithelial tumor-specific. The similar antiproliferative effectiveness of human and porcine JDK-AP suggests that these protective control mechanisms are conserved during embryonal development.

Though JDK-AP are of neural origin, they are also capable of modulating epithelial, mesenchymal and leukemic cell proliferation suggesting that, in addition to their local effect, they may also have a multi-targeted role during development. Indeed, kidney morphogenesis, for example, is dependent on expression of nerve growth factor receptors (Alley et al., 1988, *Cancer Res.* 45, 589–601).

The antiproliferative effect of porcine JDK-AP1, but not JDK-AP2 is expressed in the late (70-day), but not the early (40-day) spinal cord. We also found that early human neural tissue explants and semi-purified JDK-AP in culture suppressed hCG secretion by placental explants, while stimulating the same at 11 to 12 weeks (Barnea, et al., 1989, *Placenta* 10, 331–344; Shurtz-Swirski, et al., 1991, *Placenta* 12, 521–531). Overall, gestational age-dependence in JDK-AP's expression might reflect a transition from a cell proliferation and differentiation stage to that of organ development.

The high MW porcine JDK-AP1 appears to be a protein of 10 to 15 kDa size which has been purified almost to homogeneity by several chromatographic steps.

JDK-AP was effective with no direct toxicity: 1) following culture, cells remained viable and, in the case of MCF-7, cell morphology changed (FIG. 16); 2) JDK-AP's action was time dependent with maximal effects noted after 4 d in vitro; 3) subcutaneous injection of semi-purified human JDK-AP to x-ray-irradiated mice had no apparent adverse effect after 3 w; 4) JDK-AP, being of embryonal origin, are not likely to have toxic effects on embryo-like cells, i.e. tumors.

Evidence suggests that JDK-AP2 is not Interleukin-6 (IL6) since it is not recognized by a polyclonal antibody against IL6. Further data suggests that JDK-AP1 is not IL6. TGF-βI, a 25 kDa homodimer, is a prototype of a large GF family which is secreted as a latent complex and is involved in cell proliferation and morphogenesis (Sariola, et al., 1991, *Science* 254, 571–573; Barnard, et al., 1990, *Biochim. Biophys. Acta* 1032, 79–87; Massague, & Laiho, 1992, in *Growth Factors of the Vascular and Nervous Systems*, eds. Lenfant, C., Paoletti, R. & Albertini, A. (Karger, Basel Munchen), pp. 6–16). Several lines of indirect evidence argue against JDK-AP as being a member of the TGF-β family: 1) In our experiments, the 23 to 30 kDa region fractions affected only Balb/c 3T3 cell proliferation (FIG. 13); 2) The size of JDK-AP appears to be lower, i.e. ~10–15 and ~4.5 IcDa; 3) Contrary to our data on the inhibitory effect of JDK-AP on Rat-1 cells, TGF-B was shown to promote the proliferation of this cell line (Barnard, et al., 1990, *Biochim. Biophys. Acta* 1032, 79–87) and, 4) JDK-AP is active in the presence of DT7 which argues against a homodimer; however, only sequencing of the protein will enable direct confirmation of this evidence.

It is of note that, with the exception of the human embryonal brain whose effect was stimulatory, the total extract had no effect on cell proliferation, while separated fractions became active. Therefore, embryonal tissues contain both cell proliferation inhibitors and promoters that maintain the delicate balance between these two opposing but vital forces both of which are necessary for embryonal development. We reported that in vivo maternal exposure to teratogens during embryogenesis impairs the normal embryo-placental relationship in vitro by modifying embryonal secretary products (Shurtz-Swirski, et al., 1992, *Human Reprod.* 7, 300–304). Therefore, we hypothesize that the imbalance of the proliferative and antiproliferative factors caused by various adverse factors may lead to pregnancy dysfunction. The absence of embryo in molar pregnancy might also contribute to the known trophoblastic invasiveness due to deficient expression of JDK-AP.

We reported that the early placenta activates carcinogens in vitro (Barnea & Avigdor, 1990 *J. Steroid Biochem.* 35, 327–331; Barnea & Avigdor, 1991, *Gynecol. Obstet. Invest.* 32, 4–9). However, embryonal tumor development is rare in spite of the rapid rate of cell proliferation which could easily facilitate mutations as well as malignancy. In our view, quinone reductase and other enzymes may exert a protective role through local carcinogen/mutagen inactivation (Barnea & Avigdor, 1990, *J. Steroid Biochem.* 35, 327–331; Avigdor, et al., 1992 *Reprod. Toxicol.*, 6, 363–366). JDK-AP, combined with local metabolic protection and immune response, may be part of an intricate system which helps to maintain pregnancy (Nahhas & Barnea, 1990, *Am. J. Reprod. Immunol.* 22, 105–108; Barnea, et al., 1986, *Arch. Gynecol.* 237, 187–190; Sanyal, et al., 1989, *Am. J. Obstet. Gynecol.* 161, 446–453; Clark, 1988, in *Early Pregnancy Loss Mechanisms and Treatment*, eds. Beard, R. W. & Sharp, F. (RCOG, London), pp. 215–227).

Thus, pregnancy can be paralleled to a state of "controlled cancer." However, pregnancy, unlike cancer, can be rejected at any stage, i.e. early by spontaneous abortion or later by delivery. Cancer development following embryogenesis might actually represent an incomplete regression to the embryonal stage when cell proliferation is maximal, cell differentiation is minimal, and the body's ability to control cell proliferation is impaired.

Various publications are cited herein which are hereby incorporated by reference in their entireties.

What is claimed is:

1. A protein extract having antiproliferative properties prepared by a method comprising the following steps:

(a) solubilizing a mixture of (i) visceral organs or neural organs or a mixture of visceral and neural organs collected from a mammalian embryo and (ii) a physiologically compatible solution;

(b) centrifuging the solubilized organs to produce a pellet and a supernatant and collecting the supernatant;

(c) selecting material from the supernatant that has a molecular weight less than about 10,000 daltons;

(d) subjecting the material to chromatographic separation and collecting fractions of the separated material; and (e) testing the ability of a fraction to inhibit the cell proliferation, thereby identifying that fraction or fractions which have antiproliferative properties;

wherein the protein extract inhibits the proliferation of a MCF-7 cell in culture.

2. A protein extract having antiproliferative properties prepared by a method comprising the following steps:

(a) solubilizing a mixture of (i) visceral organs or neural organs or a mixture of visceral and neural organs collected from a mammalian embryo and (ii) a physiologically compatible solution;

(b) centrifuging the solubilized organs to produce a pellet and a supernatant and collecting the supernatant;

(c) selecting material from the supernatant that has a molecular weight less than about 8,000 daltons;

(d) subjecting the material to chromatographic separation and collecting fractions of the separated material; and (e) testing the ability of a fraction to inhibit the cell proliferation, thereby identifying that fraction or fractions which have antiproliferative properties;

wherein the protein extract inhibits the proliferation of a MCF-7 cell in culture.

* * * * *